US006887847B2

(12) United States Patent
Montelaro et al.

(10) Patent No.: US 6,887,847 B2
(45) Date of Patent: May 3, 2005

(54) VIRUS DERIVED ANTIMICROBIAL PEPTIDES

(75) Inventors: Ronald C. Montelaro, Wexford, PA (US); Timothy A. Mietzner, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 10/079,075

(22) Filed: Feb. 19, 2002

(65) Prior Publication Data

US 2002/0188102 A1 Dec. 12, 2002

Related U.S. Application Data

(63) Continuation-in-part of application No. 09/785,058, filed on Feb. 16, 2001, which is a continuation-in-part of application No. 09/785,059, filed on Feb. 16, 2001.

(51) Int. Cl.$^7$ .......................... A61K 38/00; A01N 25/08

(52) U.S. Cl. ............................... 514/2; 514/13; 514/14; 530/300; 435/174; 424/409; 623/1.1

(58) Field of Search ............................... 514/2, 13, 14; 530/300; 435/174; 424/409; 623/1.1

(56) References Cited

U.S. PATENT DOCUMENTS

| 5,714,577 A | 2/1998 | Montelaro et al. |
| 5,945,507 A | 8/1999 | Montelaro et al. |

OTHER PUBLICATIONS

Honig, B. (1999) Protein folding: from the levinthal paradox to structure prediction. J. Mol. Biol. vol. 293, pp. 283–293. Review.*
Kalia, V.et al.(2003) Rational site–directed mutations of the LLP1 and LLP–2 lentivirus lytic peptide domains in the intracytoplasmic tail of human immunodeficiency virus type 1 gp41 . . . , J. Virol. vol. 77, pp. 3634–3646.*
File,TM. "Overview of Resistance in the 1990s", Chest. 115:3S–8S. Mar. 1999 Supplement.
Friedrich et al., "Salt–Resistant Alpha–Helical Cationic Antimicrobial Peptides", Antimicrobial Agents and Chemotherapy, 43: 1542–1548, 1999.
Hancock. R.E., "Host Defence (Cationic) Peptides: What Is Their Future Clinical Potential?", Drugs, 57: 469–473, Adis International Limited, 1999.
Scott, Yan, and Hancock, "Biological Properties of Structurally Related V–Helical Cationic Antimicrobial Peptides", Infection & Immunity, 67: 2005–2009, Apr. 1999.
Tencza et al., "Lentivirus–derived antimicrobial peptides: increased potency by sequence engineering and dimerization", Journal of Antimicrobial Chemotherapy, 44: 33–41, 1999.

Beary et al., "Interruption of T–Cell signal transduction by lentivirus lytic peptides from HIV–1 transmembrane protein", Journal of Peptide Research, 51: 75–79, 1998.
Hwang and Vogel, "Structure–function relationships of antimicrobial peptides", Biochem. Cell Biol., 76: 235–246, 1998.
Comardelle et al., "A Synthetic Peptide Corresponding to the Carboxy Terminus of Human Immunodeficiency Virus Type 1 Transmembrane Glycoprotein Induces Alterations in the Ionic Permeability of Xenopus laevis Oocytes", AIDS Research & Human Retroviruses, 13: No. 17, pp. 1525–1532, 1997.
Ganz and Lehrer, "Antimicrobial peptides of leukocytes", Current Opinion in Hematology, 4: 53–58, 1997.
Tencza et al., "Novel Antimicrobial Peptides Derived from Human Immunodeficiency Virus Type 1 and Other Lentivirus Transmembrane Proteins", Antimicrobial Agents & Chemotherapy, 41: 2394–2398, 1997.
Tencza et al., "Calmodulin–Binding Function of LLP Segments from the HIV Type 1 Transmembrane Protein Is Conserved among Natural Sequence Variants", AIDS Research & Human Retroviruses, 13: No. 3, 263–269, 1997.
Arroyo et al., "Membrane Permeabilization by Different Regions of the Human Immunodeficiency Virus Type 1 Transmembrane Glycoprotein gp41", J. Virol. 69: 4095–4102, 1995.
Tencza et al., "Effect of Amino Acid Substitutions on Calmodulin Binding and Cytolytic Properties of the LLP–1 Peptide Segment of Human Immunodeficiency Virus Type 1 Transmembrane Protein", Journal of Virology, 69: 5199–5202, 1995.
Yuan et al., "Characterization of the Calmodulin Binding Domain of SIV Transmembrane Glycoprotein by NMR and CD Spectroscopy", Biochemistry, 34: 10690–10696, 1995.
Zanetti, Gennaro and Romeo, "Cathelicidins: a novel protein family with a common propregion and a variable C–terminal antimicrobial domain", FEBS Letters, 374:1–5, 1995.

(Continued)

Primary Examiner—Karen Cochrane Carlson
Assistant Examiner—Samuel Wei Liu
(74) Attorney, Agent, or Firm—Baker Botts LLP

(57) ABSTRACT

The invention is directed to peptides having antimicrobial activity (antimicrobial peptides). The antimicrobial peptides of the present invention are analogs of the Lentivirus Lytic Peptide 1 (LLP1) amino acid sequence. The invention is further directed to peptides referred to as the Lytic Base Unit (LBU) peptides derived from the LLP1 analogs, also having antimicrobial activity. In addition, the present invention is also directed to methods of using the peptides in a variety of contexts, including the treatment or prevention of infectious diseases. The antimicrobial LLP1 analog peptides and the LBU peptides (collectively eLLPs) may be highly active under high salt conditions and in biologic fluids. In addition, the eLLPs are effective when presented either in soluble form, or when attached to a solid surface. Furthermore, the peptides of the present invention are selectively active against a wide variety of bacterial pathogens and exhibit minimal toxicity to eukaryotic cells in vitro and in vivo.

30 Claims, 13 Drawing Sheets

OTHER PUBLICATIONS

Merrifield et al., "Design and synthesis of antimicrobial peptides", Antimicrobial Peptides, Ciba Foundation Symposium, , 5–6, 1994.

Moore et al., "Preliminary Experimental Anticancer Activity of Cecropins", *Peptide Research,* 7:265–269, 1994.

Miller et al., "Identification of a Calmodulin–Binding and Inhibitory Peptide Domain in the HIV–1 Transmembrane Glycoprotein", 1993, *AIDS Research and Human Retroviruses,* 9: 1057–1066.

Miller et al., "Alterations in Cell Membrane Permeability by the Lentivirus Lytic Peptide (LLP–1) of HIV–1 Transmembrane Protein", *Virology,* 196: 89–1000, 1993.

Blondelie et al., "Design of Model Amphipathic Peptides Having Potent Anitmicrobial Activities", *Biochemistry,* 31:12688–12694, 1992.

Srinivas et al., "Membrane Interactions of Synthetic Peptides Corresponding to Amphopathic Helical Segments of the Human Immunodeficiency Virus Type–1 Envelope Glycoprotein", *Journal of Biological Chemistry,* 267:7121–7127, 1992.

Wild et al., "A synthetic peptide inhibitor of human immunodeficiency virus replication: Correlation between solution structure and viral inhibition", *Proc. Natl. Acad. Sci. USA,* 89: 10537–10541, 1992.

Fontenot et al., "A Survey of Potential Problems and Quality Control in Peptide Synthesis by the Fluorenylmethoxycarbonyl Procedure", *Peptide Research,* 4:19–25, 1991.

Miller et al., "A Structural Correlation Between Lentivirus Transmembrane Proteins and Natural Cytolytic Peptides", *AIDS Research & Human Retroviruses,* 7:511–519, 1991.

Eisenberg and Wesson, "The Most Highly Amphiphilic ∀–Helics Include Two Amino Acid Segments in Human Immunodeficiency Virus Glycoprotein 41", *Biopolymers,* 29: 171–177, 1990.

Eisenberg et al., "The hydrophobic moment detects periodicity in protein hydrophocity", *Proc. Natl. Acad. Sci. U.S.A.,* 81:140–144, 1984.

Chou et al., "Prediction of The Secondary Structure of Proteins From Their Amino Acid Sequence", *Adv Enz Relat Areas Mol Bio,* 47: 45–146, 1978.

Garnier et al., "Analysis of the Accuracy and Implications of Simple Methods for Predicting the Secondary Structure of Globular Proteins", *J. Mol. Biol.,* 120: 97–120, 1978.

* cited by examiner

Figure 1

LLP1: R VIEVVQGACRA IRHI PRRIRQGLER I L

SA-5: R VIRVVQRACRA IRHI VRRIRQGLRR I L

LSA- 5: R VIRVVQRACRA IRHI VRRIRQGLRR I LRVV

WLSA5:RWIRVVQRWCRAIRHIWRRIRQGLRRWLRVV

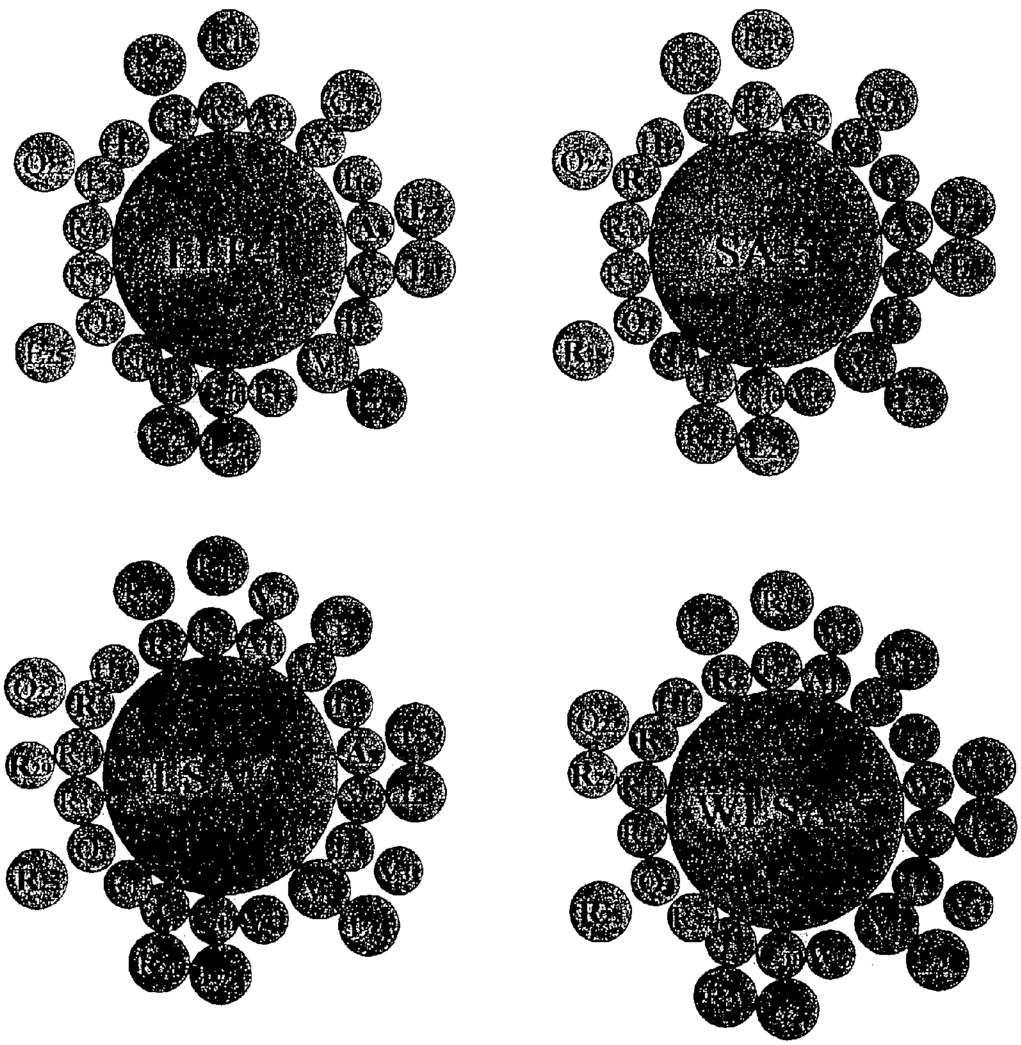

| | |
|---|---|
| LBU-1 | RVVRVVRRVVRR(SEQ ID NO:4) |
| LBU-2 | RRVVRRVRRVVRRVVRVVRRVVRR (SEQ ID NO: 5) |
| LBU-3 | VRRVVRRVVRVVRRVVRRVRRVVRRVVRVVRRVVRR (SEQ ID NO: 6) |
| LBU-3.5 | RRVVRRVRRVVRRVVRVVRRVVRRVRRVVRRVVRVVRRVVRR (SEQ ID NO:7) |
| LBU-4 | RVVRVVRRVVRRVRRVVRRVVRVVRRVVRRVRRVVRRVVRVVRRVVRR (SEQ ID NO:8) |
| WLBU-1 | RVVRVVRRWVRR (SEQ ID NO:9) |
| WLBU-2 | RRWVRRVRRVWRRVVRVVRRWVRR (SEQ ID NO:10) |
| WLBU-3 | VRRVWRRVVRVVRRWVRRVRRVWRRVVRVVRRWVRR (SEQ ID NO:11) |
| WLBU-4 | RVVRVVRRWVRRVRRVWRRVVRVVRRWVRRVRRVWRRVVRVVRRWRVV (SEQ ID NO:12) |

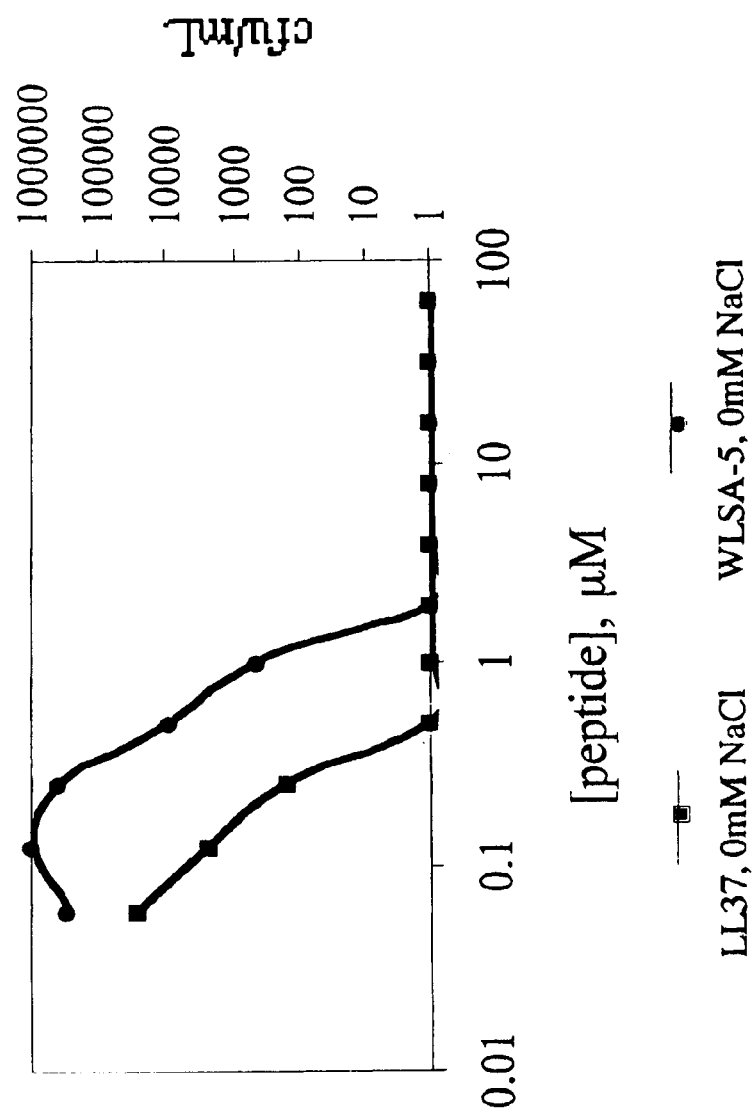
Figure 3. Killing of *P. aeruginosa* by LL37 & WLSA-5 in 10 mM PB

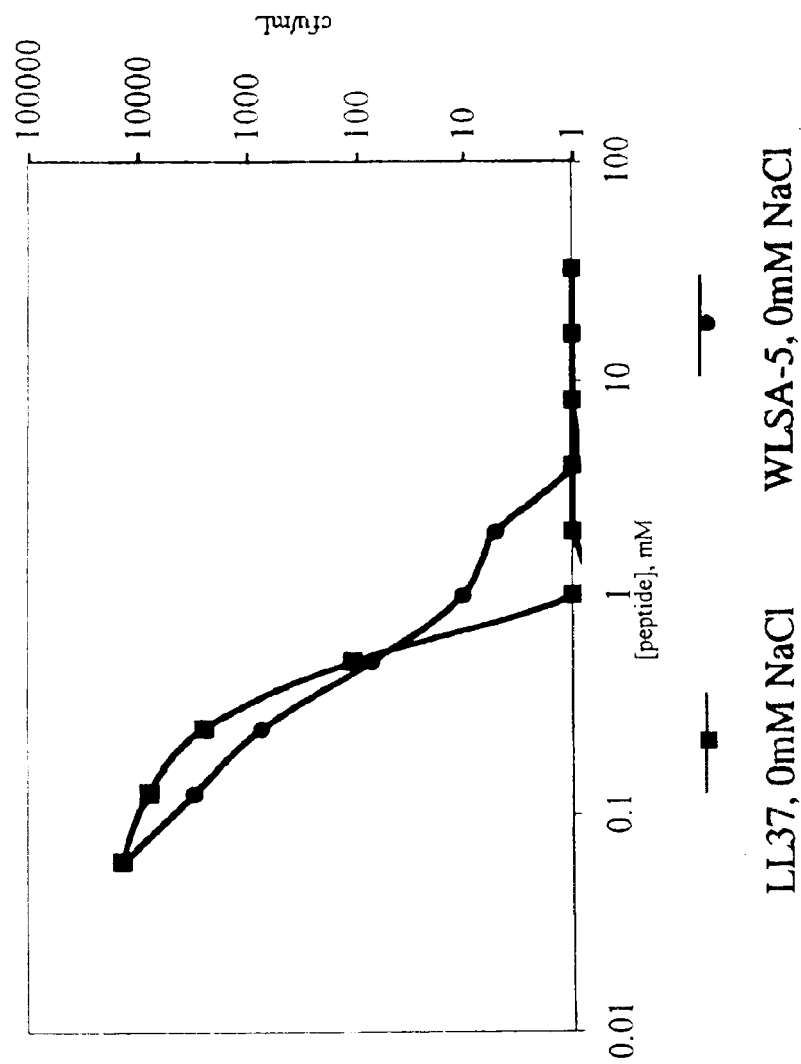
Figure 4. Killing of *S. aureus* by LL37 & WLSA-5 in 10 mM PB

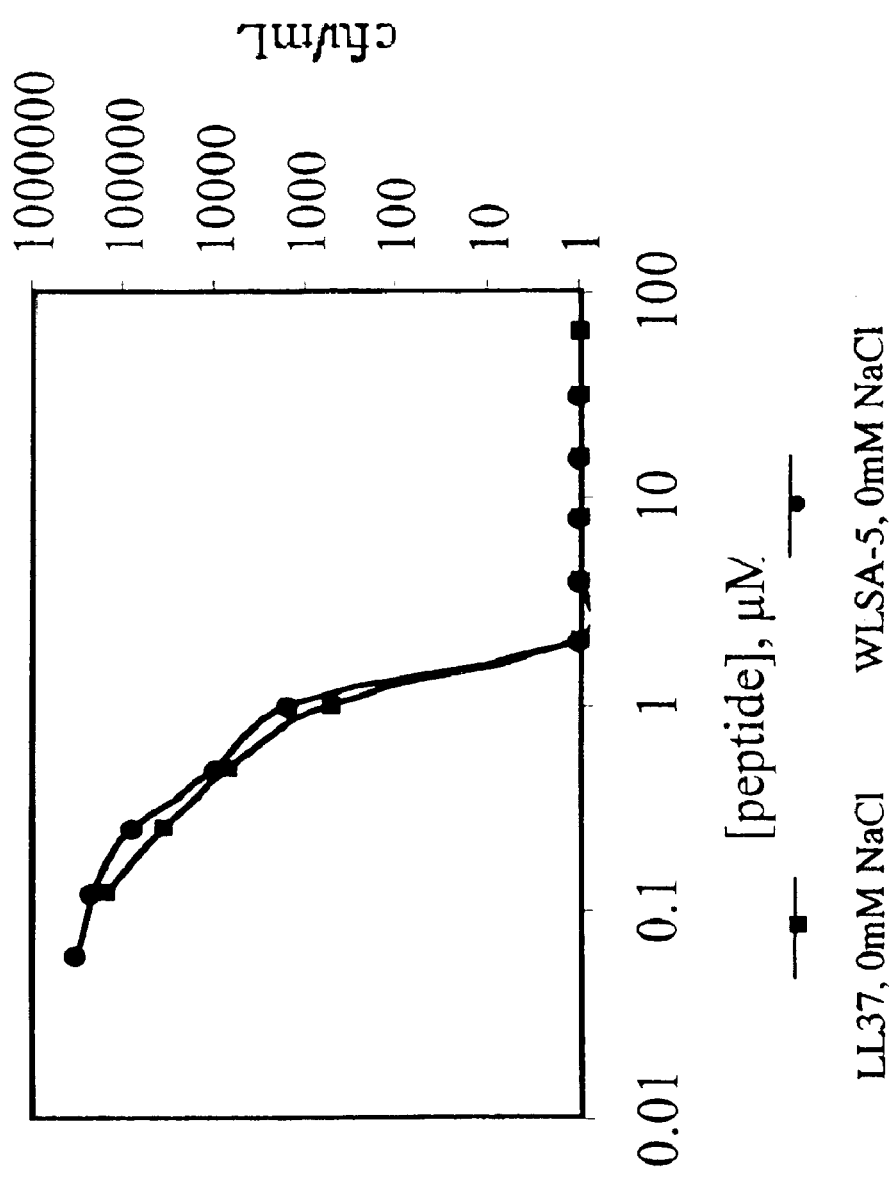
Figure 5. Killing of *P. aeruginosa* by LL37 & WLSA-5 in 10 mM PB plus 150 mM NaCl

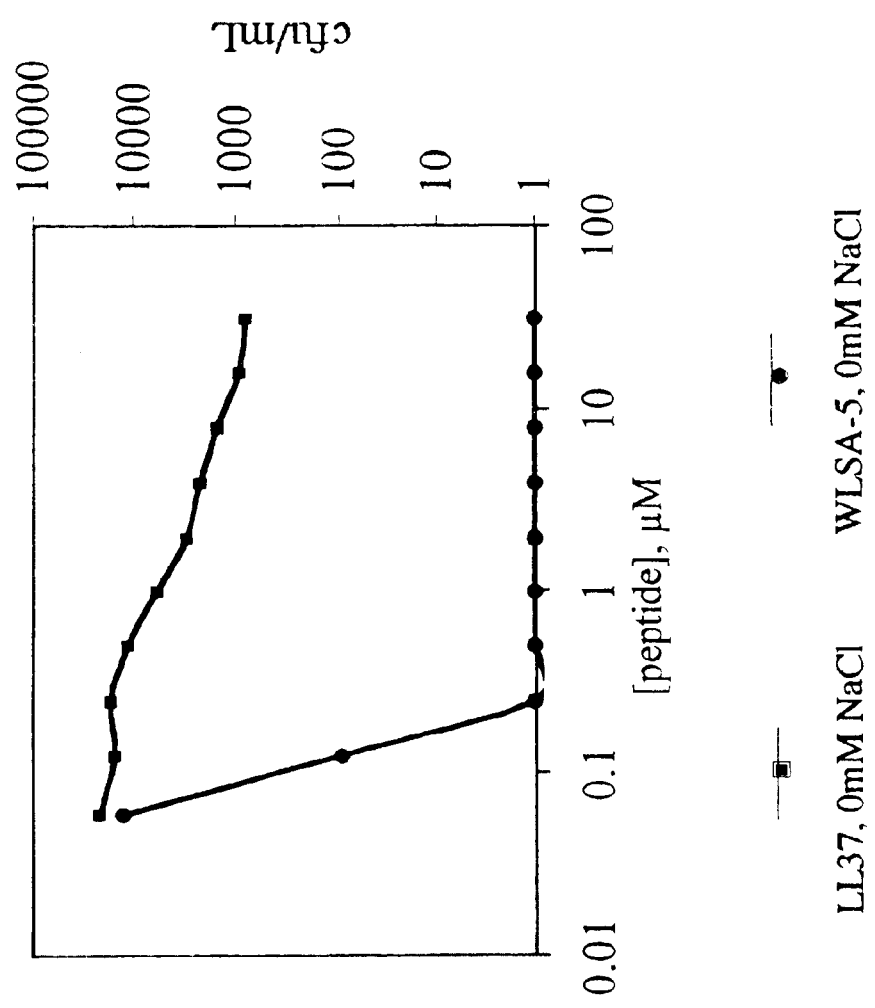
Figure 6. Killing of *S. aureus* by LL37 & WLSA-5 in 10 mM PB plus 150 mM NaCl Figure 7. Activity of LSA-5 versus WLSA-5 against *Burkholderia cepacia*

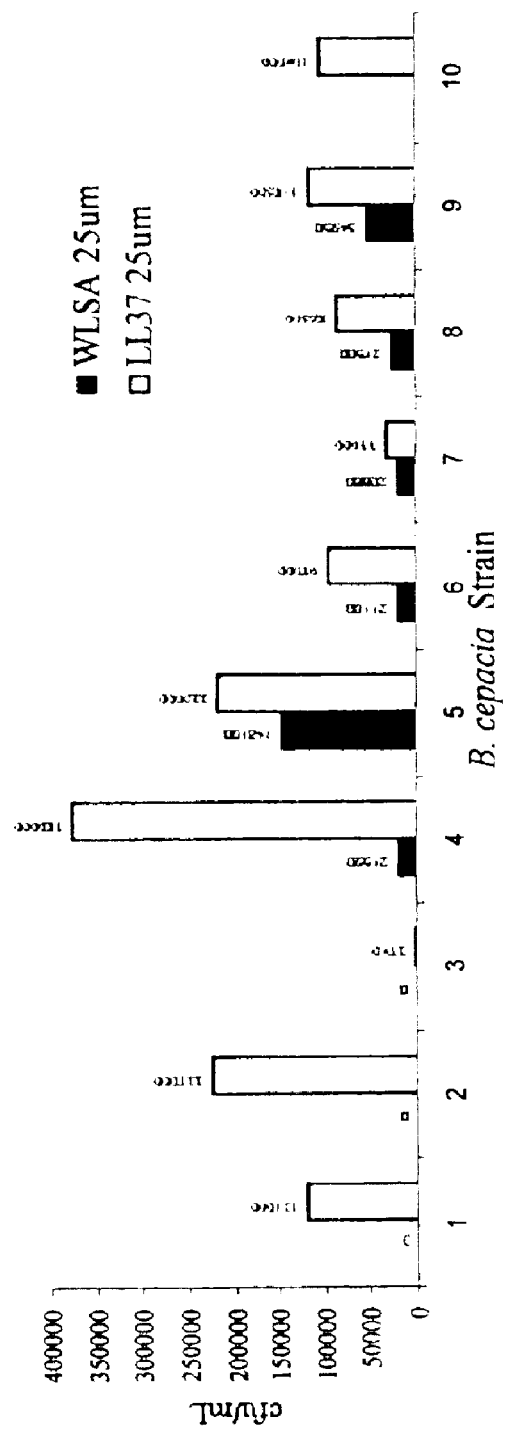
Figure 8. Antibacterial activity of WLSA-5 and the host derived LL37 against 10 different strains of *B. cepacia* representing multiple genomovars.

Figure 9. Selective toxicity of WLSA-5 for *P. aeruginosa* bound to CF human bronchial epithelial cells in culture

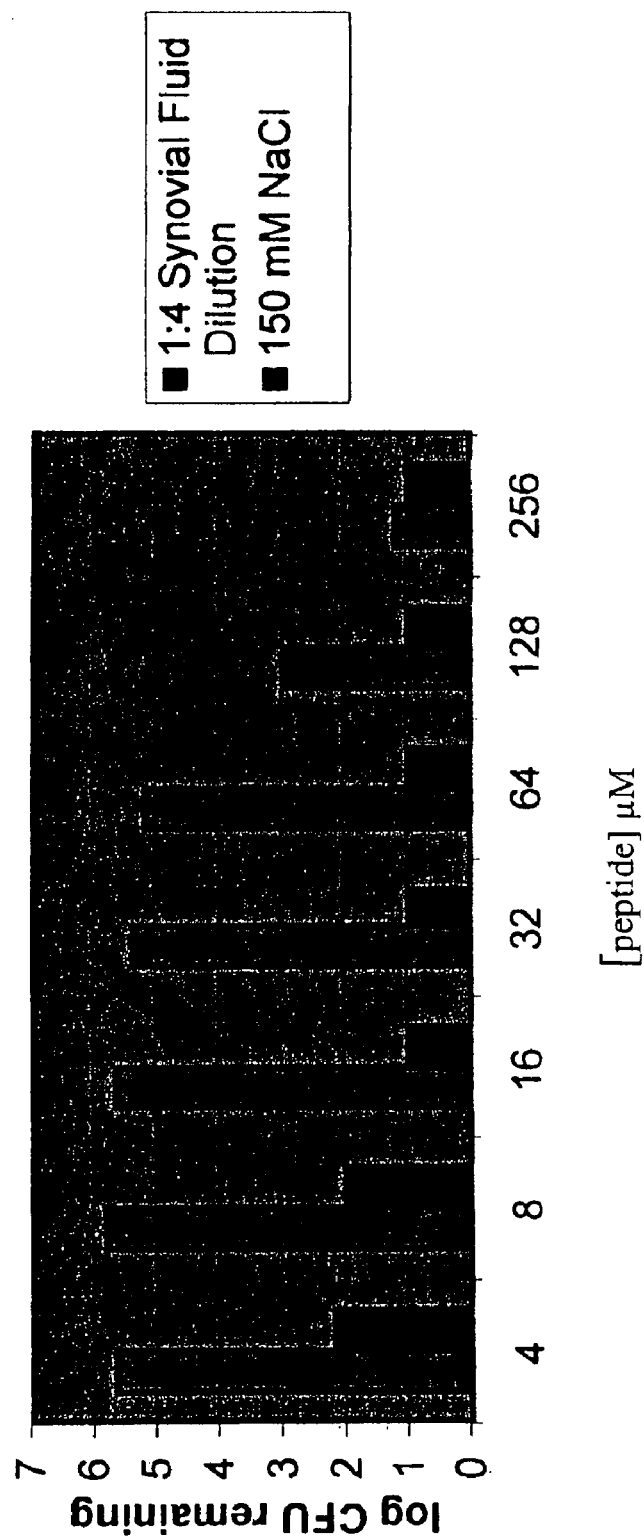
Figure 10. *In vitro* killing of *S. aureus* by WLSA-5 in synovial fluid

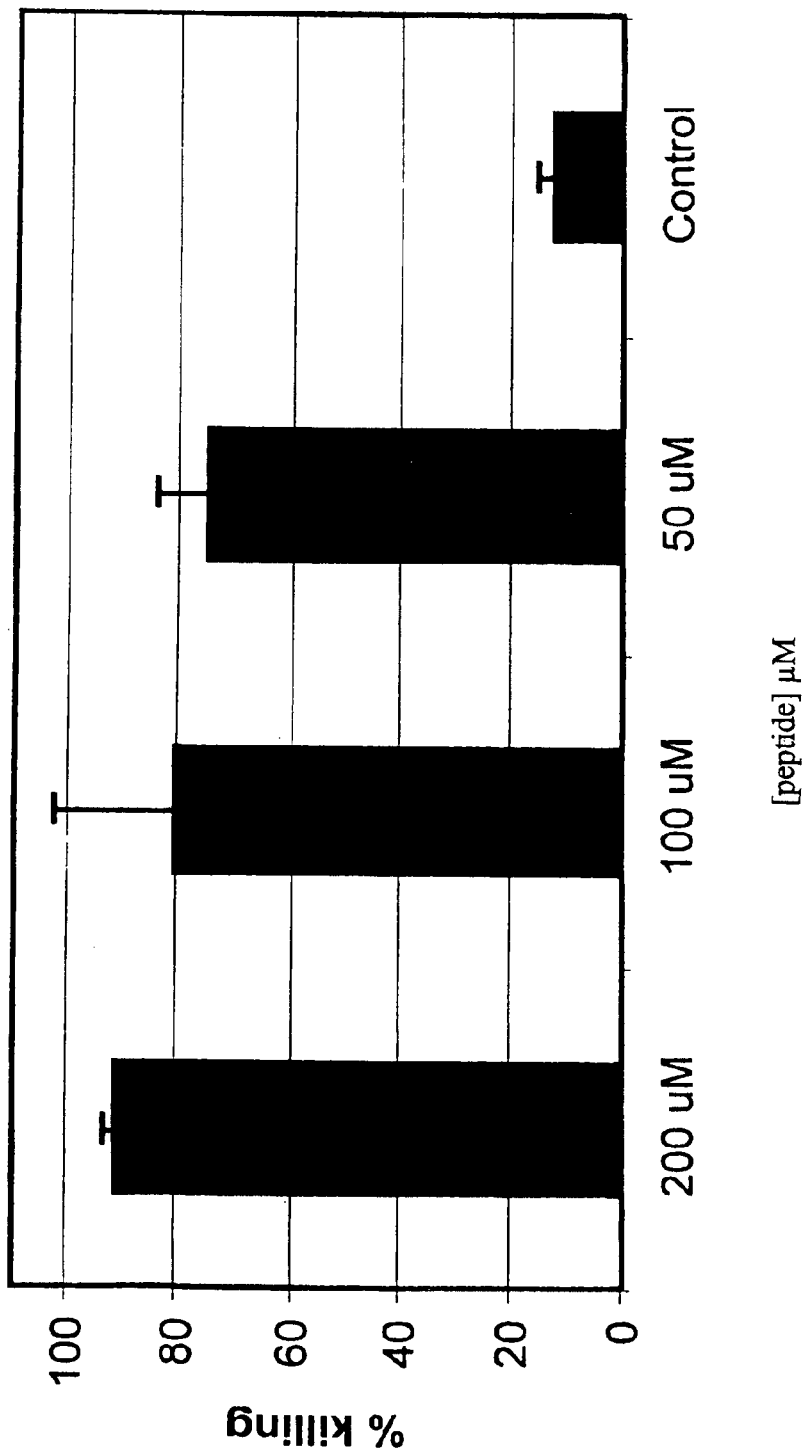
Figure 11. Dose dependent decrease in bacterial killing relative to the untreated control

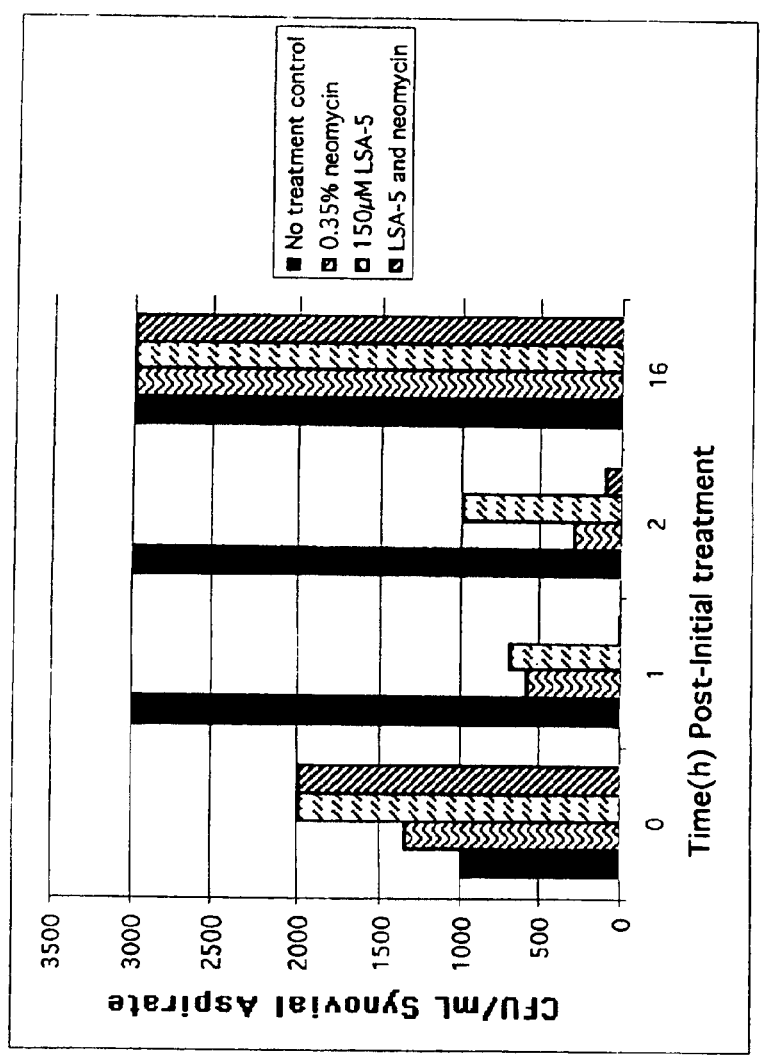
Figure 12. LSA-5/neomycin bacterial killing in rabbit joint model

SEQUENCE LISTING

<160> NUMBER OF SEQ ID NOS: 12

<210> SEQ ID NO 1
<211> LENGTH: 28
<212> TYPE: PRT
<213> ORGANISM: Artificial Sequence
<220> FEATURE:
<223> OTHER INFORMATION: Artificial peptide derived from HIV-1

<400> SEQUENCE: 1

Arg Val Ile Arg Val Val Gln Arg Ala Cys Arg Ala Ile Arg His Ile
1               5                   10                  15

Val Arg Arg Ile Arg Gln Gly Leu Arg Arg Ile Leu
            20                  25

<210> SEQ ID NO 2
<211> LENGTH: 31
<212> TYPE: PRT
<213> ORGANISM: Artificial Sequence
<220> FEATURE:
<223> OTHER INFORMATION: Artificial peptide derived from HIV-1

<400> SEQUENCE: 2

Arg Val Ile Arg Val Val Gln Arg Ala Cys Arg Ala Ile Arg His Ile
1               5                   10                  15

Val Arg Arg Ile Arg Gln Gly Leu Arg Arg Ile Leu Arg Val Val
            20                  25                  30

```
<210> SEQ ID NO 3
<211> LENGTH: 31
<212> TYPE: PRT
<213> ORGANISM: Artificial Sequence
<220> FEATURE:
<223> OTHER INFORMATION: Artificial peptide derived from HIV-1

<400> SEQUENCE: 3

Arg Trp Ile Arg Val Val Gln Arg Trp Cys Arg Ala Ile Arg His Ile
1               5                   10                  15

Trp Arg Arg Ile Arg Gln Gly Leu Arg Arg Trp Leu Arg Val Val
            20                  25                  30

<210> SEQ ID NO 4
<211> LENGTH: 12
<212> TYPE: PRT
<213> ORGANISM: Artificial Sequence
<220> FEATURE:
<223> OTHER INFORMATION: Artificial peptide derived from HIV-1

<400> SEQUENCE: 4

Arg Val Val Arg Val Val Arg Arg Val Val Arg Arg
1               5                   10

<210> SEQ ID NO 5
<211> LENGTH: 24
<212> TYPE: PRT
<213> ORGANISM: Artificial Sequence
<220> FEATURE:
<223> OTHER INFORMATION: Artificial peptide derived from HIV-1

<400> SEQUENCE: 5

Arg Arg Val Val Arg Arg Val Arg Arg Val Arg Arg Val Val Arg
1               5                   10                  15

Val Val Arg Arg Val Val Arg Arg
            20

<210> SEQ ID NO 6
<211> LENGTH: 36
<212> TYPE: PRT
<213> ORGANISM: Artificial Sequence
<220> FEATURE:
<223> OTHER INFORMATION: Artificial peptide derived from HIV-1

<400> SEQUENCE: 6

Val Arg Arg Val Val Arg Arg Val Val Arg Val Val Arg Val Val
1               5                   10                  15

Arg Arg Val Arg Arg Val Val Arg Val Val Arg Val Val Arg Arg
            20                  25                  30

Val Val Arg Arg
        35

<210> SEQ ID NO 7
<211> LENGTH: 42
<212> TYPE: PRT
<213> ORGANISM: Artificial Sequence
<220> FEATURE:
<223> OTHER INFORMATION: Artificial peptide derived from HIV-1

<400> SEQUENCE: 7

Arg Arg Val Val Arg Arg Val Arg Arg Val Arg Arg Val Val Arg
1               5                   10                  15

Val Val Arg Arg Val Val Arg Arg Val Arg Arg Val Val Arg Arg Val
```

```
            20                  25                  30

Val Arg Val Val Arg Arg Val Val Arg Arg
        35                  40

<210> SEQ ID NO 8
<211> LENGTH: 48
<212> TYPE: PRT
<213> ORGANISM: Artificial Sequence
<220> FEATURE:
<223> OTHER INFORMATION: Artificial peptide derived from HIV-1

<400> SEQUENCE: 8

Arg Val Val Arg Val Val Arg Arg Val Arg Val Arg Arg Val
1               5                   10                  15

Val Arg Arg Val Val Arg Val Val Arg Arg Val Arg Val Arg Arg Val
                20                  25                  30

Arg Val Val Arg Val Val Arg Val Val Arg Arg Val Val Arg Arg
        35                  40                  45

<210> SEQ ID NO 9
<211> LENGTH: 12
<212> TYPE: PRT
<213> ORGANISM: Artificial Sequence
<220> FEATURE:
<223> OTHER INFORMATION: Artificial peptide derived from HIV-1

<400> SEQUENCE: 9

Arg Val Val Arg Val Val Arg Arg Trp Val Arg Arg
1               5                   10

<210> SEQ ID NO 10
<211> LENGTH: 24
<212> TYPE: PRT
<213> ORGANISM: Artificial Sequence
<220> FEATURE:
<223> OTHER INFORMATION: Artificial peptide derived from HIV-1

<400> SEQUENCE: 10

Arg Arg Trp Val Arg Arg Val Arg Arg Val Trp Arg Arg Val Val Arg
1               5                   10                  15

Val Val Arg Arg Trp Val Arg Arg
                20

<210> SEQ ID NO 11
<211> LENGTH: 36
<212> TYPE: PRT
<213> ORGANISM: Artificial Sequence
<220> FEATURE:
<223> OTHER INFORMATION: Artificial peptide derived from HIV-1

<400> SEQUENCE: 11

Val Arg Arg Val Trp Arg Arg Val Val Arg Val Val Arg Arg Trp Val
1               5                   10                  15

Arg Arg Val Arg Arg Val Trp Arg Arg Val Val Arg Val Val Arg Arg
                20                  25                  30

Trp Val Arg Arg
        35

<210> SEQ ID NO 12
<211> LENGTH: 48
<212> TYPE: PRT
<213> ORGANISM: Artificial Sequence
<220> FEATURE:
<223> OTHER INFORMATION: artificial peptides derived from HIV-1
```

```
<400> SEQUENCE: 12

Arg Val Arg Val Val Arg Arg Trp Val Arg Arg Val Arg Arg Val
1               5                   10                  15

Trp Arg Arg Val Val Arg Val Val Arg Arg Trp Val Arg Arg Val Arg
            20                  25                  30

Arg Val Trp Arg Arg Val Val Arg Val Val Arg Arg Trp Arg Val Val
            35                  40                  45
```

VIRUS DERIVED ANTIMICROBIAL PEPTIDES

This application is continuation-in-part of U.S. patent application Ser. Nos. 09/785,058 of Montelaro et al., filed Feb. 16, 2001, and 09/785,059 of Montelaro et al., filed Feb. 16, 2001 which are incorporated herein by reference.

BACKGROUND OF THE INVENTION

The development of antimicrobial agents has led to a significant decrease in morbidity and mortality from infectious diseases in this century. This important public health contribution has been largely due to the widespread use of antibiotics that target specific nutrient, cell wall, DNA, RNA and protein biosynthetic pathways that are peculiar to pathogenic bacteria. However, in recent years the capacity to manage infectious diseases has been threatened by the emergence of bacterial strains that are no longer susceptible to currently available antimicrobial agents (see Files, 1999, *Chest*. 115:3S–8S). Maintenance of the public heath mandates that new antimicrobial agents need to be developed to counter these emerging resistant bacteria in order for effective infectious disease management procedures to remain in place.

A heterogeneous group of host-derived antimicrobial peptides have drawn attention as possible new therapeutic agents (see Hancock, R. E., 1999, *Drugs* 57:469–473). These peptides play an important role in innate vertebrate immunity against infection. For example, cationic antimicrobial peptides constitute as much as 18% by weight of total neutrophil protein. They are also found in high concentrations on damaged mucosal surfaces. In general these host-derived cationic peptides fit into one of four structural categories: (i) β-sheet structures that are stabilized by multiple disulfide bonds (e.g., human defensin-1), (ii) covalently stabilized loop structures (e.g., bactenecin), (iii) tryptophan (Trp)-rich, extended helical peptides (e.g., indolicidin), and (iv) amphipathic ∀-helices (e.g., the magainins and cecropins) (see Hwang and Vogel, 1998, *Biochemistry & Cell Biology* 76:235–246). Recently a new class of antimicrobial peptides, the cathelicidins, that utilize all of these structural motifs and are clearly important in host defense against infection has been described (Ganz and Lehrer, 1997, *Current Opinion in Hematology* 4:53–58).

The cathelicidins are a remarkably diverse collection of molecules that derive from prepropeptides sharing a highly conserved N-terminal propeptide segment that have been described in humans, cattle, sheep, rabbits, mice, and pigs (see Hwang and Vogel, 1998, *Biochemistry & Cell Biology* 76:235–246). The conserved propeptide segment of approximately 100 amino acids shares sequence similarity with the porcine protein cathelin, a putative cysteine protease inhibitor, hence the family name. The C-terminal domain encodes an antimicrobial peptide motif similar to one of those described above, depending upon the host and tissue that it is associated with. Cathelicidins are stored in neutrophil granules as propeptides (lacking antimicrobial activity in this form), with neutrophil activation leading to elastase-mediated endoproteolytic cleavage and generation of the C-terminal antimicrobial peptide. The human cathelicidin, referred to alternatively as FALL-39, hCAP18, LL-37, or CAMP, in its processed (active) form is a 37-amino acid amphiphilic α-helical cationic peptide (see Zanetti, Gennaro and Romeo, 1995, *FEBS Letters* 374:1–5). Expression of LL-37 has been detected in human neutrophils, testicular cells, respiratory epithelia, and in keratinocytes at sites of inflammation.

The amphipathic cationic peptides of the α-helical class demonstrate minimal bactericidal concentrations (MBCs) in the μg/mL range (levels equivalent to other antimicrobial agents) and are able to kill a broad range of gram-negative and gram-positive bacterial pathogens, including those that are highly resistant to multiple antibiotics (see Hancock, R. E., 1999, *Drugs* 57:469–473). The mechanism by which these peptides kill bacteria proceeds in a two step process by first binding to the negatively charged bacterial surface and driving these bound peptides into the bacterial membrane, thereby disrupting its structural integrity. For gram-negative organisms, cationic antimicrobial peptides have the added advantage of binding lipopolysaccharide (LPS), thereby detoxifying its endotoxic activity (see Scott, Yan, and Hancock, 1999, *Infection & Immunity* 67:2005–2009). The hallmark of amphipathic cationic α-helical antimicrobial peptides is their capacity to fold into an amphipathic secondary structure that presents a hydrophilic face with a net positive charge of at least +2. A number of different amino acid sequence combinations allow a peptide to achieve this characteristic structure. Consequently, hundreds of host-derived amphipathic cationic α-helical peptides have been described to date all showing limited sequence homology at the level of primary sequence comparison (see Hwang and Vogel, 1998, *Biochemistry & Cell Biology* 76:235–246).

In contrast to host derived antimicrobial peptides, which have evolved with the express purpose of killing bacteria, a novel class of antimicrobial peptides derived from discrete segments of the lentiviral transmembrane (TM) protein cytoplasmic tail has been described that have not evolved for the same purpose as host-derived peptides (see Beary et al., 1998, *Journal of Peptide Research* 51:75–79; Comardelle et al., 1997, *AIDS Research & Human Retroviruses* 13:1525–1532; Miller et al., 1993, *AIDS Research & Human Retroviruses* 9:1057–1066; Miller et al., 1993, *Virology* 196:89–1000; Tencza et al., 1995, *Virology* 69:5199–5202; Tencza et al., 1997, *Antimicrobial Agents & Chemotherapy* 41:2394–2398; Tencza et al., 1997, *AIDS Research & Human Retroviruses* 13:263–269; Yuan et al., 1995, *Biochemistry* 34:10690–10696). These peptides are referred to as lentiviral lytic peptides (LLPs) with the prototypical LLP being LLP1 (amino acids 828–856 of the HIV-1 viral isolate HXB2R Env). LLP1 is derived from the 28-residues encoded by the C-terminal portion of the HIV-1 TM protein that, when modeled as an α-helix, demonstrates amphipathic character with clearly delineated cationic and hydrophobic faces. Among the many antimicrobial peptides currently described in the literature, LLP1 is most homologous chemically to the magainins and the human cathelicidin, LL37.

LLP1 has been studied for its calmodulin-binding and antibacterial properties. LLP1 binds to host cell $Ca^{2+}$-saturated calmodulin with near nanomolar affinity and this property has been correlated with the inhibition of T-cell activation, suggesting that these peptides may dampen an inflammatory response (see Beary et al., 1998, *Journal of Peptide Research* 51:75–79; Miller et al., 1993, *AIDS Research & Human Retroviruses* 9:1057–1066; Tencza et al., 1995, *Virology* 69:5199–5202; Tencza et al., 1997, *AIDS Research & Human Retroviruses* 13:263–269; Yuan et al., 1995, *Biochemistry* 34:10690–10696). LLP1 antibacterial activity has been investigated by surveying diverse gram-negative and -positive bacterial isolates. This analysis demonstrates that LLP1 has antibacterial activity which is equal to, or more potent than magainin-2. These isolates included methicillin and vancomycin resistant strains as well as other strains that were highly resistant to multiple antibiotics (see Tencza et al., 1997, *Antimicrobial Agents & Chemotherapy*

41:2394–2398). The lysis of bacteria by LLP1 is rapid, nearly sterilizing a suspension of 1×10⁵ colony-forming units of *Pseudomonas aeruginosa* or *Staphylococcus aureus* within 60 seconds of exposure (see Tencza et al., 1997, *Antimicrobial Agents & Chemotherapy* 41:2394–2398). The mechanism of LLP1 action is thought to perturb negatively charged bacterial membranes, and to a lesser extent, neutral mammalian cell membranes. The predilection of the peptide for bacterial cells over mammalian cell membranes forms the basis for its selective toxicity.

Single amino acid changes in the LLP1 profoundly affect its calmodulin binding and antibacterial activity (see Tencza et al., 1995, *Virology* 69:5199–5202; Tencza et al., 1999, *Journal of Antimicrobial Chemotherapy* 44:33–41). In general, amino acid substitutions in the LLP1 parent sequence of basic residues to acidic residues decrease both calmodulin binding and bactericidal activities. Similarly, altering single hydrophobic residues to hydrophilic residues also decreased both of these activities. Furthermore, dimerization through disulfide bond formation of a single Cys found within the LLP1 parent sequence significantly increased its activity for *S. aureus* (see Tencza et al., 1999, *Journal of Antimicrobial Chemotherapy* 44:33–41). Finally, decreasing the length of the LLP1 dimer to 21 residues (peptide bis-TL1) reduced its red blood cell lysis activity without significantly reducing its antibacterial activity (see Tencza et al., 1999, *Journal of Antimicrobial Chemotherapy* 44:33–41). These data suggest that the LLP1 parent sequence can be engineered for increased potency and selectivity. The potential for this engineering forms the basis for this invention.

SUMMARY OF THE INVENTION

The present invention is directed to peptides having antimicrobial activity ("antimicrobial peptides"). In one embodiment of the invention three antimicrobial peptides which are derived from, and are analogs of, the LLP1 peptide parent sequence corresponding to amino acids 828–856 of the HIV-1 viral isolate HXB2R Env have been described and include SA-5 (SEQ ID NO:1), LSA-5 (SEQ ID NO:2) and WLSA-5 (SEQ ID NO:3) (see Table 1 below). The antimicrobial activity of other LLP1 peptide analogues has been previously described (see Tencza et al., 1999, *Journal of Antimicrobial Chemotherapy* 44:33–41, U.S. Pat. No. 5,714,577 of Montelaro et al. and U.S. Pat. No. 5,945,507 of Montelaro et al.).

In another embodiment of the invention, the antimicrobial peptides are LLP1 analogs having modifications based on the following principles: (i) optimizing amphipathicity, (ii) substituting arginine (Arg) on the charged face and/or valine (Val) or tryptophan (Trp) on the hydrophobic face with another amino acid, and (iii) increasing peptide length (referred to collectively herein as Lytic Base Unit peptides (LBU peptides), e.g. LBU-2, SEQ ID NO:4; LBU-3, SEQ ID NO:5; LBU-3.5, SEQ ID NO:6; LBU-4, SEQ ID NO:7; WLBU-1, SEQ ID NO:8, WLBU-2, SEQ ID NO:9, WLBU-3, SEQ ID NO:10; and WLBU-4, SEQ ID NO:11; see Table 1). The LBU peptides deviate greatly from the parent LLPI, for example, LBU-2 and LBU-3 deviate from the parent LLP1 sequence by greater than 90%.

TABLE 1

| | | |
|---|---|---|
| SA-5: | RVIRV VQRAC RAIRH IVRRI RQGLR RIL | (SEQ ID NO:1) |
| LSA-5: | RVIRV VQRAC RAIRH IVRRI RQGLR RILRV V | (SEQ ID NO:2) |
| WLSA-5: | RWIRV VQRWC RAIRH IWRRI RQGLR RWLRV V | (SEQ ID NO:3) |
| LBU-1 | RVVRV VRRVV RR | (SEQ ID NO:4) |
| LBU-2: | RRVVR RVRRV VRRVV RVVRR VVRR | (SEQ ID NO:5) |
| LBU-3: | VRRVV RRVVR VVRRV VRRVR RVVRR VVRVV RRVVRR | (SEQ ID NO:6) |
| LBU-3.5 | RRVVR RVRRV VRRVV RVVRR VVRRV RRVVR RVVRV VRRVV RR | (SEQ ID NO:7) |
| LBU-4 | RVVRV VRRVV RRVRR VVRRV VRVVR RVVRR VRRVV RRVVR VVRRV VRR | (SEQ ID NO:8) |
| WLBU-1 | RVVRV VRRWV RR | (SEQ ID NO:9) |
| WLBU-2 | RRWVR RVRRV WRRVV RVVRR WVRR | (SEQ ID NO:10) |
| WLBU-3 | VRRVW RRVVR VVRRW VRRVR RVWRR VVRVV RRWVR R | (SEQ ID NO:11) |
| WLBU-4 | RVVRV VRRWV RRVRR VWRRV VRVVR RWVRR VRRVW RRVVR VVRRW RVV | (SEQ ID NO:12) |

The LLP1 analogue peptides and the LBU peptides (collectively referred to herein as "engineered LLPs" (eLLPs)) of the present invention have a broader spectrum of activity (i.e., the ability to kill highly resistant bacteria) and increased potency (i.e., lowering the molar concentration required to kill bacteria) when compared with previously described LLP1 analogs. The eLLPs of the present invention are highly inhibitory to microorganisms under physiologic salt concentrations, function in the presence of synovial fluid, and demonstrate only minimal toxicity in animal models. As a result, the eLLPs may be defined as selective antimicrobial agents. In addition, the peptides of the present invention function by disrupting bacterial membranes and are active when bound to a solid phase. The ability of these peptides to maintain activity when bound to a solid phase is a significant advantage over conventional antibiotics in that these peptides may be useful as coatings on sterile devices such as prostheses or catheters where it would be advantageous to prevent bacterial biofilm nucleation.

BRIEF DESCRIPTION OF THE DRAWINGS

The present invention may be better understood with reference to the attached drawings of which FIG. 1 shows the sequences of the engineered LLPs (eLLPs) SA-5 (SEQ ID NO:1), LSA-5 (SEQ ID NO:2), and WLSA-5 (SEQ ID NO:3) relative to the parent LLP1 sequence.

FIG. 3 shows the activity of the peptide WLSA-5 (SEQ ID NO:3) in comparison with LL37 against *P. aeruginosa* in the standard broth dilution assay employing phosphate buffer (low salt conditions).

FIG. 4 demonstrates the activity of the peptide WLSA-5 (SEQ ID NO:3) in comparison with LL37 against *S. aureus* in the standard broth dilution assay employing phosphate buffer (low salt conditions).

FIG. 5 shows the activity of the peptide WLSA-5 (SEQ ID NO:3) in comparison with LL37 against *P. aeruginosa* in the standard broth dilution assay employing phosphate buffer containing 150 mM NaCl (physiologic salt conditions).

FIG. 6 shows the activity of the peptide WLSA-5 (SEQ ID NO:3) in comparison with LL37 against *S. aureus* in the standard broth dilution assay employing phosphate buffer containing physiologic NaCl.

FIG. 7 demonstrates in a standard broth dilution model that WLSA-5 (SEQ ID NO:3) is more active than LSA-5 against *Burkholderia cepacia*, a notoriously antibiotic resistant bacterium associated advanced cystic fibrosis lung infection.

FIG. 8 compares the ability of 25 µM WLSA-5 (SEQ ID NO:3) or LL37 to kill multiple genomovars of *B. cepacia*. In this experiment, a standard inoculum of each organism was exposed to a single concentration (25 µM) of WLSA-5 and LL37 and the reduction in colony forming units determined.

FIG. 9 shows the antibacterial activity of WLSA-5 (SEQ ID NO:3) against *Pseudomonas aeruginosa* attached to differentiated human bronchial epithelial cells in comparison with LL37, the host derived antimicrobial peptide found in the airway surface fluid. This data demonstrates that WLSA-5 is active in this model of cystic fibrosis lung infection. The circles measure % Rte (% change in transepithelial resistance). The squared measure the surviving bacteria.

FIG. 10 is a bar graph comparing the bactericidal activity of LSA-5 (SEQ ID NO:2) against *S. aureus* in a 1:4 dilution of human synovial fluid (light bars) and compares it with killing in phosphate buffer containing physiologic NaCl. The data suggests that components of synovial fluid limit the activity of the peptide, but that it is still active at 128 µM.

FIG. 11 demonstrates that, in the rabbit joint sepsis model, administration of LSA-5 (SEQ ID NO:2) at 50, 100 and 150 µM significantly increases bacterial killing.

FIG. 12 illustrates that in the rabbit joint sepsis model, LSA-5 (SEQ ID NO:2) is functional and nearly as effective as a standard concentration of neomycin at reducing the bacterial load within the joint. When used in combination with neomycin, a maximal decrease in bacterial load was observed.

DETAILED DESCRIPTION

Figure 2:
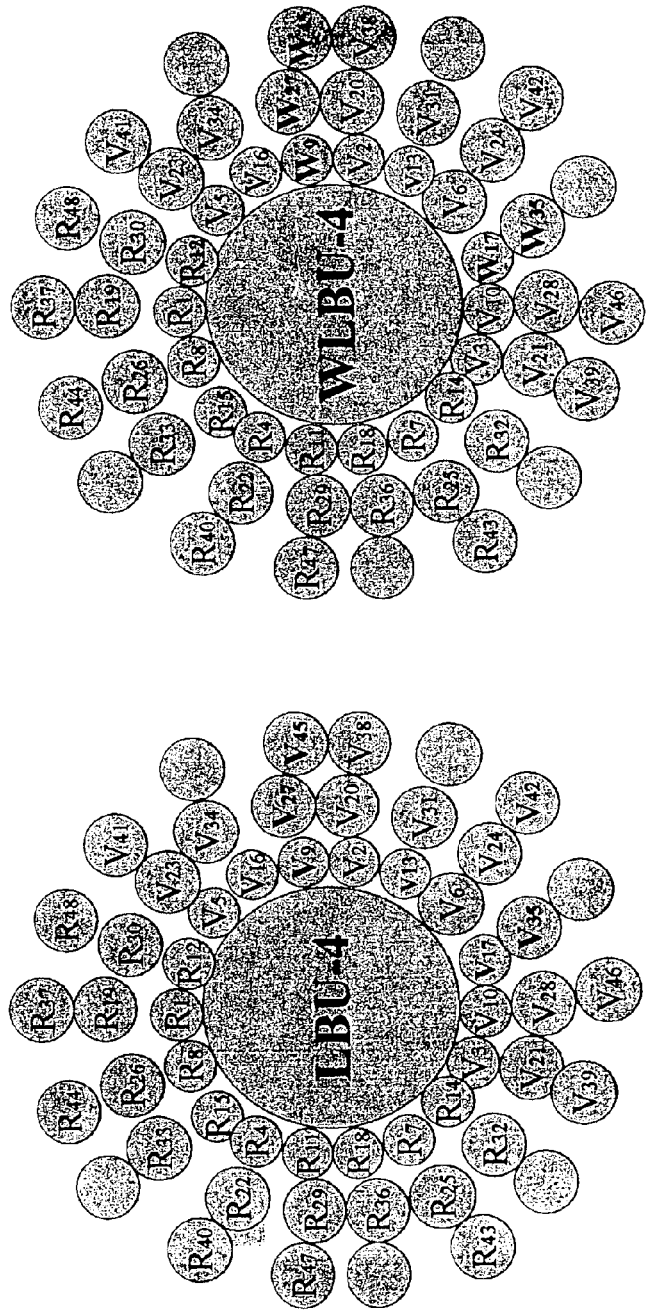
FIG. 2 shows the sequences of the engineered LBU peptides (SEQ ID NOs:4–12).

Since reporting the antibacterial activity of the LLP1 (see Tencza et al., 1997, *Antimicrobial Agents & Chemotherapy* 41:2394–2398), a number of different LLP1 analogues have been prepared (see, e.g. U.S. Pat. No. 5,714,577 of Montelaro et al. and U.S. Pat. No. 5,945,507 of Montelaro et al. and Tencza et al., 1999, *Journal of Antimicrobial Chemotherapy* 44:33041) by manipulating the parent sequence to increase potency (i.e., increase their molar bacterial killing activity) and broaden the spectrum of activity against clinical isolates. This has been achieved by optimizing the hydrophilic and hydrophobic faces of the modeled α-helix. The present invention is directed to three antimicrobial peptides, which are LLP1 peptide analogs, SA-5 (SEQ ID NO:1), LSA-5 (SEQ ID NO:2) and WLSA-5 (SEQ ID NO:3) (see Table 1 above). In addition, the present invention is directed to antimicrobial peptides which are LLP1 analogs having modifications based on the following principles: (i) optimizing amphipathicity, (ii) substituting with Arg on the charged face and Val on the hydrophobic face, (iii) increasing peptide length, and (iv) periodically substituting Val with Trp (referred to collectively herein as LBU peptides, e.g. LBU-1 (SEQ ID NO:4) LBU-2, SEQ ID NO:5; LBU-3, SEQ ID NO:6; LBU-3.5, SEQ ID NO:7; LBU-4, SEQ ID NO:8; WLBU-1, SEQ ID NO:9; WLBU-2, SEQ ID NO:10; WLBU-3, SEQ ID NO:11; and WLBU-4, SEQ ID NO:12, see Table 1). The LLP1 peptide analogs and the LBU peptides of the present invention are referred to herein as eLLPs. The composition of SA-5 (SEQ ID NO:1). LSA-5 (SEQ ID NO:2), WLSA-5 (SEQ ID NO:3). LBU-4 (SEQ ID NO:7) and WLBU-4 (SEQ ID NO:12) is described in FIGS. 1 and 2 with regard to their primary sequences when modeled as an α-helical structure and compared with the parent peptide LLP 1.

The peptide designated SA-5 substitutes three arginine residues for a glycine (Gly) and two glutamic acid (Glu) residues that model on the hydrophilic face of the LLP1 parent sequence, and a valine (Val) to proline (Pro) substitution that models on the hydrophobic face of this sequence. The rationale underlying the generation of this peptide is to optimize the cationic, amphipathic character of the original LLP1 sequence.

The peptide designated LSA-5 contrasts previous reports describing the potency of truncated derivatives of LLP1 (see Tencza et al., 1999, *Journal of Antimicrobial Chemotherapy* 44:33041) by investigating the activity of LLP derivatives of increased length. LSA-5 extends the length of the modeled α-helix by one turn and preserves the amphipathic, Arg-rich cationic character.

Based on the structural studies of Hwang and Vogel (*Biochemistry & Cell Biology* 76:235–246 (1998)), Trp residues have been shown to intercalate optimally into bacterial membranes. However, the fact that Trp may intercalate into biologic membranes does not imply that specific peptides containing Trp will selectively disrupt bacterial membranes. The WLSA-5 peptide was derived by replacing four residues on the hydrophobic face of LSA-5 with Trp residues.

In addition, the present invention is directed to LLP analog peptides comprising modifications based on the following principles: (i) optimizing amphipathicity, (ii) substituting with Arg on the charged face and Val on the hydrophobic face, (iii) increasing peptide length, and (iv) periodically substituting Val with Trp. Peptides modified according to these principles are referred to herein as the Lytic Base Unit (LBU) peptides. For example, the peptides LBU-2 and LBU-3 were formulated as a polymer of Arg and Val residues designed to create maximal amphipathic α-helical character with a length of at least 24 residues.

The antimicrobial activity of the peptides of the present invention is discussed below in the Examples.

The antimicrobial peptides of the present invention are unique in their sequences and the sources from which they were derived. It would not be obvious that subtle alterations in the previously reported LLP1 sequence and increasing peptide length could dramatically improve potency and spectrum of activity. Furthermore, LBU peptides are completely engineered and not based on any native sequences.

The activity of the eLLPs SA-5 (SEQ ID NO:1), LSA-5 (SEQ ID NO:2), WLSA-5 (SEQ ID NO:3), LBU-1 (SEQ ID NO:4); LBU-2 (SEQ ID NO:5), LBU-3 (SEQ ID NO:6), LBU-3 (SEQ ID NO:7), LBU-4(SEQ ID NO:8), WLBU-1 (SEQ ID NO:9), WLBU-2 (SEQ ID NO:10), WLBU-3 (SEQ ID NO:11) and WLBU-4 (SEQ ID NO:12) against a range of bacteria including *Staphylococcus aureus*, methicillin-resistant *S. aureus*, and *Pseudomonas aeruginosa* is summarized in Table 2 below.

Table 2 indicates the MBCs of peptides expressed in nanomolar concentrations. These results demonstrate the antimicrobial potency of these eLLPs. The activity of these peptides compares favorably with other antibacterial peptides which may have equal or decreased activity (as indicated by a higher minimum bactericidal concentration (MBC, see Example 2 below). Table 2 indicates the MBCs of eLLPs against different organisms and at different salt conditions (expressed in nanomolar).

TABLE 2

| Peptide | Psuedomonas aeruginosa | | Staphylococcus aureus | | Methicillin Resistant S. aureus | |
|---|---|---|---|---|---|---|
| | 0 mM NaCl | 150 mM NaCl | 0 mM NaCl | 150 mM NaCl | 0 mM NaCl | 150 mM NaCl |
| LLP1 | 1000 | 1000 | 8000 | 16000 | 16000 | — |
| SA-5 | 1000 | 1000 | 1000 | — | — | — |
| LSA-5 | 800 | 800 | 1000 | 1000 | 150 | — |
| WLSA-5 | 1000 | 1000 | 1000 | 1000 | 150 | — |
| LBU-2 | 1500 | 800 | 1500 | >100,000 | — | — |
| LBU-3 | 1500 | 800 | 1500 | 1500 | — | — |
| LBU-3.5 | 400 | 400 | 1000 | 600 | 1500 | 200 |
| LBU-4 | 800 | 400 | 800 | 800 | — | — |
| WLBU-1 | 400 | 2500 | 30,000 | 10,000 | 50,000 | 50,000 |
| WLBU-2 | 200 | 100 | 1000 | 600 | 200 | 100 |
| WLBU-3 | 1500 | 800 | 3,000 | 600 | 400 | 100 |
| WLBU-4 | 1500 | 400 | 3,000 | 600 | 1500 | 200 |

The antimicrobial peptides of the present invention, collectively referred to herein as "eLLPs", exhibit antimicrobial activity against diverse microorganisms, and are analogs of the LLP1 peptide corresponding to amino acids 828–856 of the HIV-1 viral isolate HXB2R Env TM. The eLLPs comprise Arg-rich sequences, which, when modeled for secondary structure, display high amphipathicity and hydrophobic moment. The eLLPs are highly inhibitory to microorganisms, but significantly less toxic to mammalian cells. As a result, these peptides can be characterized as selective antimicrobial agents. In addition, the eLLPs of the present invention include LLP1 peptide analogs comprising modifications based on the following principles: (i) optimizing amphipathicity, (ii) substituting Arg on the charged face and/or Val or Trp on the hydrophobic face, and (iii) increasing peptide length, collectively referred to herein as LBU peptides.

As used herein, the term "antimicrobial" refers to the ability of the peptides of the invention to prevent, inhibit or destroy the growth of microbes such as bacteria, fungi, protozoa and viruses. As used herein, the term "peptide" refers to an oligomer of at least two contiguous amino acids, linked together by a peptide bond.

The eLLPs of this invention are structural and functional analogs of the parent peptide, LLP1, that exhibits selective toxicity for microorganisms. As used herein, the term "analog" refers to a peptide which contains substitutions, rearrangements, deletions, additions and/or chemical modifications in the amino acid sequence of parent peptide, and retains the structural and functional properties of the parent peptide.

The eLLPs of the present invention lack significant primary sequence homology to known antimicrobial non-LLP peptides (e.g., magainins or the cathelicidins). The eLLPs are rich in positively charged residues and are predicted to form an amphipathic α-helix. The amphipathic α-helix imparts a unique and potent antimicrobial activity to the peptides of the present invention. The structural properties defining the antimicrobial peptides of the invention include, inter alia, the ability to form three-dimensional amphipathic α-helical structures (Eisenberg and Wesson, 1990, *Biopolymers* 29:171–177). The amphipathic α-helical structure comprises residues arranged such that 3.6 amino acid residues complete one turn of the helix. Based on this arrangement, which is based on well known protein folding constraints, an estimate of amphipathicity may be made by examination of the amino acid sequence.

In one embodiment of the invention, optimization of this "ideal" amphipathic α-helical motif is one of the principles used to generate the eLLPs of this invention. In another embodiment of the invention, the substitution of Arg residues on the hydrophilic face and Trp or Val residues on the hydrophobic face is one of the principles used to generate the eLLPs of the present invention. The antimicrobial peptides of the invention may further contain Ala, Gly, Ile, or Phe and other amino acid residues that can be tolerated within a general amphipathic α-helical structure. These residues may impart a structure, which enhances the potency and selectivity of a peptide in a manner that can only be determined empirically. Some eLLPs of the invention contain one Cys which, by virtue of its capacity to form a disulfide bond, can confer increased potency to a peptide containing such a residue as a disulfide-linked dimeric peptide (e.g., bis-eLLP). The position of the Cys lies on the interface of the hydrophilic and hydrophobic faces of the amphipathic α-helical structure when modeled as such. The placement of such Cys residues would not be obvious to someone skilled in the art and must be determined empirically. This may be accomplished by a person of skill in the art without undue experimentation, e.g. by using a computer modeling of peptide structure. For example, Computer modeling programs such as "Helical Wheel" (Genetics Computer Group, Madison, Wis.) may be used to design the peptides of the present invention. In a further embodiment, the length of the peptides of the present invention may be increased to improve their antimicrobial activity.

The eLLPs of the present invention are unique in their functional properties. The unique structure of the antimicrobial peptides imparts high potency while maintaining selectivity for bacteria. The potency of the antimicrobial peptides compares very favorably to that of magainin or cathelicidin. eLLPs rapidly kill both gram-positive and gram-negative bacteria, demonstrating a broad spectrum of activity including but not limited to, gram-positive bacteria such as *Listeria monocytogenes, Bacillus subtilis, Enterococcus faecalis* (including vancomycin-sensitive (VSEF) and vancomycin-resistant (VREF) strains), *Enterococcus faecium* (including vancomycin-sensitive (VSEF) and vancomycin-resistant (VREF) strains), *Staphylococcus aureus* (including methicillin-sensitive (MSSA) and methicillin-resistant (MRSA) strains), *Staphylococcus epidermidis* (including methicillin-sensitive (MSSE) and methicillin-resistant (MRSE) strains), *Staphylococcus salivarius, Corynebacterium minutissium, Corynebacterium pseudodiphtheriae, Corynebacterium stratium, Corynebacterium* group G1, *Corynebacterium* group G2, *Streptococcus pneumonia* (including penicillin-resistant (PSRP) strains), *Streptococcus mitis* and *Streptococcus sanguis*; Gram-negative bacteria including *Escherichia coli, Klebsiella pneumoniae, Pseudomonas aeruginosa, Burkholderia cepacia, Serratia marcescens, Haemophilus influenzae, Moraxella* sp., *Neisseria meningitidis, Neisseria gonorrhoeae, Salmonella typhimurium, Actinomyces* spp., *Porphyromonas* spp., *Prevotella melaninogenicus, Helicobacter pylori, Helicobacter felis*, and *Campylobacter jejuni*. Functional properties also include selective antimicrobial activity with minimal toxicity for mammalian cells. Therefore, based on the teachings and guidance herein, one skilled in the art can readily design these eLLPs within the scope of the invention, which have a desired potency and selectivity.

Analogs of particular antimicrobial peptides and/or other cytolytic peptides are within the scope of the present invention. The analogs retain the structural and functional properties described herein. In another embodiment of the invention, D-amino acids may be used in place of L-amino acids and may provide increased metabolic stability, since peptides containing D-amino acids are resistant to mammalian proteases, which generally cleave peptides composed of L-amino acids. For example, cecropin analogs containing D-amino acids exhibit antibacterial activity (Merrifield et al., Antimicrobial Peptides, Ciba Foundation Symposium, Wiley, Chichester, 5–26, 1994). The present invention is also directed to peptide analogs that are longer than the LLP1 parent peptide. These peptides may be more potent than the LLP1 parent sequence when compared on a molar basis, and demonstrate a broader spectrum of activity. As discussed above, the inclusion of a Cys residue in an antimicrobial peptide is useful in facilitating the formation of intramolecular or intermolecular disulfide bonds that can stabilize a dimeric peptide and improves antimicrobial potency against certain microbial pathogens such as *S. aureus*.

The antimicrobial peptides of the present invention may be highly active under high salt conditions and in biologic fluids (see Example 4 and FIGS. 3–6). The ability of the peptides to maintain activity in physiological NaCl concentrations allows the peptides to exhibit antimicrobial activity within physiologic fluids of vertebrate hosts.

Peptides of this invention can be synthesized by classic Merrifield solid phase synthesis techniques, using manual or automated procedures known to those skilled in the art, e.g., as described by Miller et al. (*AIDS Research & Human Retroviruses* 7:511–519 (1991), using an Advanced Chemtech model 200 (Advanced Chemtech, Louisville, Ky.), or using a Millipore 9050+ (Millipore, Bedford, Mass.) automated synthesizer with Fmoc synthesis protocols (see Fontenot et al., 1991, *Peptide Research* 4:19–25), or other available instrumentation. After cleavage and deprotection, synthetic peptides can be purified by, for example, gel filtration chromatography and any reverse-phase column/ HPLC system known to those skilled in the art. Peptides may also be prepared by standard recombinant DNA technology using techniques well known to those skilled in the art for nucleotide-based peptide design (Sambrook et al., Molecular Cloning: A Laboratory Manual, 2nd edition (Cold Spring Harbor Press, Cold Spring Harbor, N.Y.; Ausubel et al., Current Protocols in Molecular Biology, John Wiley and Sons, New York, 1995). Site-directed mutagenesis or oligonucleotide synthesis, for example, may be used to prepare peptide analogs from parent peptides. The amino acid sequences of the peptides can also be confirmed and identified by amino acid composition analysis as well as manual and automated Edman degradation and determination of each amino acid, HPLC analysis, or mass spectrometry. The N-terminal amino acid of the peptides may contain a free amino group or be acetylated, and the C-terminal amino acid of the peptide may be amidated, lipidated or comprise a free carboxyl group. Other modifications of the peptide termini known to those skilled in the art are within the scope of the invention.

The criticality of particular amino acid residues in a peptide may be tested by altering or replacing the residue of interest. For example, the requirement for a Cys residue, which can be involved in the formation of intramolecular or intermolecular disulfide bonds, can be tested by mutagenesis of the Cys to another amino acid, for example, tyrosine, which cannot form such a bond. A Cys can be chemically altered so as to prevent the formation of a disulfide bond by, for example, reduction and carboxyamidation, in which an amide group is added to the sulfur atom of the cysteine (Creighton, T. E., ed., Protein Structure: A Practical Approach, IRL Press, Oxford, 1989). Conversely, a Cys residue in a peptide may be maintained in an oxidized state (that is, in the form of a disulfide bond) in order to assess whether such bonds are involved in the antimicrobial activity of a peptide. Such oxidation may be performed by, for example, an air-oxidation procedure (Ellman, G. L., *Arch. Biochem.* 82: 70–77, 1959), or by DMSO oxidation (Tam et al., *J. Am. Chem. Soc.* 113: 6657–6662, 1991). Similarly, Trp residues can be substituted on the hydrophobic face (e.g. the WLSA-5 peptide (SEQ ID NO:3)).

Computer modeling is useful to design antimicrobial peptides of the present invention based on their preferred structural properties. A standard method known in the art for prediction of amphipathic helical structure from a linear sequence is the Eisenberg algorithm (Eisenberg et al., *Biopolymers* 27: 171–177, 1990) and is useful for modeling the peptides of the present invention. Peptide sequences are analyzed for predicted secondary structure, hydrophobic moment, and amphipathicity using programs available to the skilled artisan (e.g. may be obtained from the internet). These programs which generally use algorithms that are predictive for secondary structure (Chou et al., *Adv. Enz.* 47: 45–146, 1978; Garnier et al., *J. Mol. Biol.* 120: 97, 1978) or hydrophobic moment (Eisenberg et al., *Proc. Natl. Acad. Sci. U.S.A.* 81: 140–144, 1984) may be used.

Peptide concentration is quantitated using a standard ninhydrin colorimetric assay (see Example 1 below). A standard curve using a Leu standard is generated by reading the spectrophptometric absorbance at 570 nm of increasing volumes of the leucine stock combined with the commercially available (Dupont) ninhydrin reagents on a spectrophotometer. The readings of peptide samples are compared to the leucine standard curve to quantitate the amount of peptide in each sample. Alternatively, if the peptide contains Trp in its sequence, peptide concentration can be determined by UV spectroscopy using a molar extinction coefficie $\epsilon_{280}$=5500 mol$^{-1}$·cm$^{-1}$.

The effect of the antimicrobial peptides of the present invention on the viability of prokaryotic and eukaryotic cells may be assayed by any method that determines survival after treatment or exposure to the peptides. For screening purposes, standard bacterial broth dilution assays are used and can be compared with red blood cell lysis assays (see Tencza et al., 1999, *Journal of Antimicrobial Chemotherapy* 44:33–41). However, ultimately this selective toxicity comparison should be preformed when both prokaryotic and eukaryotic cells are exposed to peptide during coincubation (i.e., under identical conditions). In addition, the effect of the antimicrobial peptides on the viability of other pathogens, including yeast, mycoplasma and viruses, may also be tested.

The antibacterial properties of the peptides of the present invention may be determined, e.g., from a bacterial lysis assay (EXAMPLE 1), as well as by other methods, including, inter alia, growth inhibition assays (Blondelie et al., *Biochemistry* 31:12688, 1992), fluorescence-based bacterial viability assays (e.g., Molecular Probes BacLight), flow cytometry analyses (Arroyo et al., *J. Virol.* 69: 4095–4102, 1995), and other standard assays known to those skilled in the art.

Determination of the antifungal properties of the peptides of the invention may be performed by techniques well known to those skilled in the art (Selitrennikoff, C., Screening for Antifungal Drugs, in Biotechnology of Filamentous Fungi, Finkelstein et al., eds., Butterworth-Heinemann, Boston, 1992). Determination of the antiviral properties of the peptides of the invention may be performed by techniques well known to those skilled in the art, for example by the ability of a peptide to inhibit viral plaque formation in standard, art recognized, in vitro assays (e.g., Wild et al., *Proc. Natl. Acad. Sci. USA* 89: 10537–10541, 1992).

The assays for growth inhibition of a microbial target can be used to derive a minimum bactericidal concentration (MBC) value for the peptide, i.e., the concentration of peptide required to kill 99.9% of the microbial sample being tested. This value is well known to those in the art as representative of the effectiveness of a particular antimicrobial agent (e.g., an antibiotic) against a particular organism or group of organisms. In assays to detect the MBC of a peptide, growth inhibition of a bacterial population also can be measured with reference to the number of colony forming units (cfu) after exposure to a peptide relative to a control experiment without a peptide.

Another parameter useful in identifying and measuring the effectiveness of the antimicrobial peptides of the invention is the determination of the kinetics of the antimicrobial activity of a peptide. Such a determination can be made by performing any of the assays of the invention and determining antimicrobial activity as a function of time. In a preferred embodiment, the peptides display kinetics that result in efficient killing of a microorganism.

The antimicrobial peptides of the invention display selective toxicity to target microorganisms and minimal toxicity to mammalian cells. Determining the toxicity of the peptides claimed in this invention on mammalian cells is preferably performed using tissue culture assays. For mammalian cells, such assay methods include, inter alia, trypan blue exclusion assays and tetrazolium-based colorimetric assays (MTT-assay). See Moore et al., 1994, *Peptide Research* 7:265–269. Where a specific cell type may release a specific metabolite upon changes in membrane permeability, that specific metabolite may be assayed, e.g., the release of hemoglobin upon the lysis of red blood cells (see Srinivas et al., 1992, *Journal of Biological Chemistry* 267:7121–7127). In addition, the disruption of the transepithelial resistance (Rte) of a cell monolayer that have formed tight junctions can be monitored (see FIG. 9). The peptides of the invention are preferably tested against primary cells, e.g., using human bronchial epithelial (HBE) cells in polarized culture, or other primary cell cultures routinely used by those skilled in the art. Permanently transformed cell lines may also be used, e.g., Jurkat cells.

In determining the therapeutic potential of an eLLP, a lower MBC for bacterial, fungal, protozoal, or viral samples relative to that observed for mammalian cells defines a selectively antimicrobial. Characterization of the antimicrobial activity of the peptides of the invention can be performed using any microorganism that can be cultured and assayed, as above, including bacteria, fungi, protozoa or viruses.

Antibacterial assays for the peptides of the invention can be performed to determine the bacterial killing activity toward both gram-positive and gram-negative microorganisms. *E. coli* and *P. aeruginosa* are examples of gram-negative organisms. *S. aureus* may be used as a model of a gram-positive microorganism, and this is a significant clinical target since most strains are refractive to most systemic antibiotic treatments. Methicillin-resistant *S. aureus* may be used as an antibiotic-resistant model organism. *E. faecalis* can be assayed, and in particular, the vancomycin-resistant isolates found in clinical settings, e.g. hospitals. *S. marcescens* is a source of ophthalmic and other topical infections, and can be readily assayed. The peptides may be used in the treatment of external ear infections (otitis externa), or in the treatment of sexually transmitted diseases such as those caused by *Neisseria gonorrhoeae*. Other bacterial pathogens, often found extracellularly on mucosal surfaces, which may be targets for the peptides of the present invention include, but are not limited to, *Streptococcus pneumonia, Streptococcus pyogenes*, Group B *Streptococci, Gardnerella vaginalis, Klebsiella pneumoniae, Acinetobacter* spp., *Haemophilus aegyptius, Haemophilus influenzae, S. epidermis, Propionibacterium acnes*, and oral pathogens such as *Actinomyces* spp., *Porphyromonas* spp., and *Prevotella melaninogenicus*. Other microbial pathogens may also be targets for these peptides and these microbial pathogens, and the infections that they cause, are known to those skilled in the art.

*Mycoplasma* belong to the class Mollicutes, eubacteria that appear to have evolved regressibly by genome reduction from gram-positive ancestors. Unlike classic bacteria, they have no cell wall but instead are bounded by a single triple-layered membrane, and may be susceptible to certain peptides of the present invention. Antimycoplasma assays may be performed to test the antimycoplasma activity of the peptides of the present invention. *Mycoplasma* human pathogens include *Mycoplasma pneumoniae* (a respiratory pathogen), *Mycoplasma hominis* (a urogenital pathogen) and *Ureaplasma urealyticum* (a urogenital pathogen). The peptides of the present invention may be used to treat diseases related to *mycoplasma* infection. In addition, *mycoplasma* contamination is a frequent problem in culturing cells in vitro and is very difficult to effectively eliminate. Therefore, the peptides of the present invention may be useful in selectively eliminating mycoplasma contamination in tissue culture.

Fungi also may be susceptible to specific peptides of the invention because their membranes contain ergosterol, which is not found in human cells. This differentiation may be exploited in therapeutic applications so as to design peptides of the invention, which selectively inhibit fungi, yet do not interfere with human or mammalian membrane function. Precedent for a mechanism of selective antifungal membrane targeting is found, for example, in the use of the antifungal agent, amphotericin B, which binds ergosterol and forms pores in the membrane (Goodman et al., The Pharmacological Basis of Therapeutics, Macmillan Publishing, New York, 1985). All fungi can be considered as potential targets of these peptides, including, but not limited to, dermatophytes, yeasts, dimorphic fungi, and filamentous molds. Specific fungal pathogens which may be targets for the peptides of the present invention include, but are not limited to, *Microsporum* spp., *Epidermophyton* spp., *Candida albicans, Cryptococcus neoformans, Trichophyton* spp., *Sporothrix schenkii* and *Aspergillus fumigatus*, as well as other pathogens known to those skilled in the art.

Both DNA and RNA viruses can be targets of the antimicrobial peptides of the invention. In a particular embodiment of the invention, an enveloped virus may be susceptible to the antiviral effect of the peptides due to their ability to target and disrupt membrane structures. While all viruses are potential targets, the enveloped viruses, such as poxvirus, herpesvirus, hepadnavirus, baculovirus, orthomyxovirus, paramyxovirus, retrovirus, togavirus. rhabdovirus, bunyavirus and flavivirus, for example, may be particularly susceptible to the antimicrobial peptides of the invention. . In a preferred embodiment of the present invention, the virus is selected from the group consisting of lentiviruses, such as HIV-1, herpes viruses, such as HSV, or orthomyxoviruses, such as influezae virus. In a particularly preferred embodiment, the virus is HIV-1 because of association with spread on a mucosal surface that could be manipulated by the topical administration of a microbicide such as a synthetic peptide that is active against HIV-1 and other sexually transmitted disease pathogens. See Example 5 below.

Additionally, further elucidation of the mechanism of the peptides and their biochemical targets may come from the use of isogenic mutants of bacteria, fungi, *mycoplasma* and viruses that are altered in cytoplasmic and/or outer wall membrane content. Peptide analogs of the invention may be specifically tested against these mutants to identify specific designs that are optimally inhibitory against particular membrane constituents.

The peptides of the present invention may be useful for inhibiting or treating a particular microbial infection, such as, but not limited to, cystic fibrosis lung infection (see Example 3 below), joint sepsis (see Example 4 below), ocular infections, periodontal disease, STDs, otitis externa, cutaneous infections, burn infections, vaginal infections, and diabetic foot ulcers.

Furthermore, the peptides of the present invention may be useful to inhibit microbial colonization. For example, the peptides may be delivered and expressed by eukaryotic cells in vivo, via transfection using viral vectors. The continued expression of the peptides in the cells and secretion into their environment may interfere with colonization of microbes and prevent microbial infection. This may be useful to prevent cystic fibrosis by delivering the peptides of the present invention to airway epithelial cells which may inhibit colonization of bacteria involved in cystic fibrosis. Cells expressing the peptides may be able to continuously combat the colonization of a range of pathogenic microbes.

The evaluation of an antimicrobial peptide of the invention for inhibiting or treating a particular microbial infection may also involve the use of animal models of infection that are acknowledged by those skilled in the art to be relevant to such infections in a human or other mammal. EXAMPLE 3 below describes a cell culture model of cystic fibrosis lung infection in which the selective toxicity of peptides may be tested. EXAMPLE 4 below describes an animal model of joint sepsis that can be used to evaluate antimicrobial peptides.

Advantages of the use of the eLLPs as antibiotics include the likelihood that it may be more difficult for a microorganism to develop a mechanism of resistance against an antibiotic that targets a membrane structure. The fact that other microbial pathogens have never been exposed to these agents (in contrast to conventional antibiotics) is an additional advantage. In view of the above noted properties of the peptides of the invention, it is contemplated that the antimicrobial peptides of the invention may be used in treating an infectious process in a host caused by a microorganism.

Systemic administration of the peptides of the present invention may induce an immunogenic response in a host. Therefore, techniques known in the art, such as waxing with polyethylene glycol, may be employed to reduce the immunogenicity of the peptides when administered systemically.

Another embodiment of this invention is the surface-active mechanism of action of these peptides that allows them to function while attached to a solid phase substrate through their N-terminal amino group. The peptides of the present invention are active when attached to a solid phase substrate (see Example 4, Table 3). Therefore, the peptides of the present invention are useful as coatings on implanted devices, such as prostheses, e.g. prosthetic joints and limbs. The peptides may also be useful as coatings on artificial organs and intraocular lenses.

The eLLPs of the present invention may have a single amino group and a free sulfhydryl group. These functional groups allow for specific attachment to a derivatized surface. For example, N-hydroxysuccinimide (NHS) chemistry can be used to attach an appropriately derivatized surface to the N-terminal amino group of the eLLPs of the present invention. Alternatively, a surface derivatized with free carboxyl groups could be cross-linked to the free sulfydryl group on the eLLP Cys residue using m-maleimidobenzyl-N-hydroxy-succinimide ester (MBS, Pierce Chemical, Rockford, Ill.). Other methods to couple peptides to derivatized surfaces are known to those skilled in the art.

In addition, the eLLPs of the present invention is directed to a peptide-cargo complex wherein the peptides of the present invention may be attached to a cargo to allow for the delivery of the cargo into a target microorganism. The cargo may comprise a factor having anti-microbial activity and may improve the potency and/or increase the antimicrobial activity of the eLLPs of the present invention. For example, the eLLPs may be cross-linked to antibacterial enzymes such as lysozyme or antibiotics, such as penicillin, to increase their potency. Other methods for attaching the peptides of the present invention to cargo are well known in the art.

Another aspect of the invention is directed to methods for eliminating an infectious process by administering the peptides of the present invention to a patient for a time and under conditions to promote healing. In a particular aspect of the invention, the high potency and rapid bactericidal activity of these peptides make them attractive candidates for use in preventive therapies, such as sterilization of wounds prior to suture, as well as the sterilization of instruments prior to their use in surgical or other invasive procedures. Their microbial specificity renders the peptides of the invention particularly useful in inhibiting unwanted microbial growth in tissue culture, especially those used for production of recombinant proteins or vectors for use in gene therapy. In another embodiment of the invention, the peptides may be used in combination formulations with one or more other drugs to facilitate delivery of a drug into a host cell or microorganism (e.g., see Example 4, FIG. 12).

The invention is also directed to physiologic compositions containing one or more of the antimicrobial peptides as the active ingredient which may be administered to a host in a therapeutically effective amount, an amount of the peptide (or combinations of peptides) sufficient to minimize or eliminate the target microorganism from a cell culture, or host individual.

The physiological compositions contain a therapeutically effective dosage of at least one of the antimicrobial peptides according to the present invention, together with a pharmaceutically acceptable carrier. The invention is also directed to methods for treating a microbial infection in a host using the compositions of the invention. Such treatment comprises the administration of a physiological composition in a therapeutically effective amount to an individual in need of such treatment. The compositions may be administered parenterally by intramuscular or intravenous routes but would most likely be most useful when administered by aerosolization, subcutaneous administration, or oral, topical and intranasal administration. Preferably, physiologic compositions containing the peptides of the invention are applied topically for the elimination of surface infections caused by microorganisms. When used in a topical pharmaceutical composition, the peptide active ingredient can be used at a concentration of 0.001 to 20% (w/v) of the composition.

When applied topically, the peptide compositions may be combined with other ingredients, such as carriers and/or adjuvants. The peptides may also be covalently attached to a protein carrier, such as albumin, or to a prosthetic implant so as to minimize diffusion of the peptides. There are no limitations on the nature of such other ingredients, except that they must be pharmaceutically acceptable, efficacious for the intended administration and cannot degrade the active ingredients of the compositions. When the peptide compositions of this invention are applied to a site of topical infection, they may act as an irritant (which would stimulate influx of scavenger cells). The peptide compositions can also be in the form of ointments or suspensions, preferably in combination with purified collagen. The peptide compositions also may be impregnated into transdermal patches, plasters and bandages, preferably in a liquid or semi-liquid form.

The peptides of the invention may also be systematically administered for promoting the healing of an infectious process. When applied systemically, the peptide compositions may be formulated as liquids, pills, tablets, lozenges or the like, for enteral administration, or in liquid form for parenteral injection. The peptides (or peptide-protein conjugates) may be combined with other ingredients such as carriers and/or adjuvants known to those skilled in the art. There are no limitations on the nature of such other ingredients, except that they must be physiologically acceptable, efficacious for their intended administration and cannot degrade the active ingredients of the compositions. The physiologic forms suitable for injection include sterile aqueous solutions or dispersions and sterile powders for the extemporaneous preparation of sterile injectable solutions or dispersions. In all cases the ultimate solution form must be sterile and fluid. Typical carriers known in the art include a solvent or dispersion medium containing, for example, water buffered aqueous solutions (i.e., biocompatible buffers), ethanol, polyol such as glycerol, propylene glycol, polyethylene glycol, suitable mixtures thereof, surfactants or vegetable oils. Sterilization can be accomplished by an art-recognized technique, including but not limited to, filtration or addition of antibacterial or antifungal agents, for example, paraben, chlorobutanol, phenol, sorbic acid or thimerosal.

Further, isotonic agents such as sugars, for example, may be incorporated in the subject compositions. Production of sterile injectable solutions containing the subject peptides is accomplished by incorporating these compounds in the required amount in the appropriate solvent with various ingredients enumerated above, as required, followed by sterilization, preferably filter sterilization.

When the peptides of the invention are administered orally, the physiologic compositions thereof containing an effective dosage of the peptide may also contain an inert diluent, an assimilable, edible carrier and the like, be in hard or soft shell gelatin capsules, be compressed into tablets, or may be in an elixir, suspension, syrup, or the like. The subject peptides are thus compounded for convenient and effective administration in pharmaceutically effective amounts with a suitable pharmaceutically acceptable carrier in a therapeutically effective dosage.

The precise effective amount of peptides to be used in the methods of this invention to control infection can be determined without undue experimentation by those skilled in the art who understand the nature of the activity of antibiotics and the nature of an infectious process. The amount of an antibiotic peptide (such as the peptides of this invention) that must be utilized can vary with the magnitude of the infection and the microorganism to be treated. The amount of peptide of the invention per unit volume of combined medication for administration may also be determined without undue experimentation by those skilled in the art. However, it can generally be stated that the peptides should preferably be present in an amount of at least about 1.0 nanogram per milliliter of combined composition, more preferably in an amount up to about 1.0 milligram per milliliter. Systemic dosages also depend on the age, weight and conditions of the patient and on the administration route. For example, a suitable dosage for the administration to adult humans can range from about 0.01 to about 100 mg per kilogram body weight. The preferred dosage can range from about 0.5 to about 5.0 mg per kilogram body weight. As used herein, a physiologically acceptable carrier includes any and all solvents, dispersion media, coatings, and the like. The use of such media and agents are well known in the art.

Because the antimicrobial peptide compositions of this invention are designed to eliminate an ongoing infectious process, a continual application or periodic reapplication of the compositions may be indicated and preferred. The practice of the invention employs, unless otherwise indicated, conventional techniques of synthetic organic chemistry, protein chemistry, molecular biology, microbiology, recombinant DNA technology, and pharmacology, which are within the skill of the art. Such techniques are explained fully in the literature (See, e.g., Scopes, R. K. Protein Purification: Principles and Practices, 2nd edition, Springer-Verlag, 1987; Methods in Enzymology, S. Colwick and N. Kaplan, editors, Academic Press; Sambrook et al., Molecular Cloning: A Laboratory Manual, 2nd edition, Cold Spring Harbor Press, Cold Spring Harbor, N.Y.; Ausubel et al., Current Protocols in Molecular Biology, John Wiley and Sons, New York, 1995; Remington's Pharmaceutical Sciences, 17th ed., Mack Publishing Co., Easton, Pa., 1985).

The following examples further illustrate the invention, but are not meant to limit the same.

EXAMPLES

Example 1

Design and Synthesis of eLLPS.

Design of eLLPs. Using the principles described above, peptide sequences were designed for synthesis based on altering the residues of the LLP1 parent sequence to create an Arg-rich hydrophilic face and a more idealized hydrophobic face of a predicted amphipathic α-helical structure. In one case, WLSA-5 (SEQ ID NO:3), Trp residues were included to increase potency and spectrum of activity (FIG. 1). For LBU-2 (SEQ ID NO:5) and LBU-3 (SEQ ID NO:6), an idealized amphipathic α-helical structure consisting of Arg residues and Val residues on the hydrophilic and hydrophobic faces, respectively, were designed and are described in FIG. 2.

Peptide Synthesis. Peptides were synthesized as described previously (see Miller, Jaynes and Montelaro, *AIDS Research & Human Retroviruses* 7:511–519 and Fontenot et al., *Peptide Research* 4:19–25) using either an Advanced Chemtech model 200 (Advanced Chemtech, Louisville, Ky.) or a Millipore 9050+ (Millipore, Bedford, Mass.) automated peptide synthesizer with Fmoc synthesis protocols. After cleavage and deprotection, synthetic peptides were characterized and purified by reverse-phase HPLC on Vydac C18 or C4 columns (The Separations Group, Hesperia, Calif.). The identity of each peptide was confirmed by mass spectrometry (University of Pittsburgh Protein & Peptide Core Facility).

Peptide Quantitation. Peptide concentrations were determined by quantitative ninhydrin assay. Briefly, to samples containing 5–60 nmol peptide, Ninhydrin Reagents A, B, and C prepared as described by Sarin et al., (*Analytical Biochemistry* 117:147–157) were added. A leucine standard solution, calibrated by routine amino acid composition analysis, consisting of 0–60 nmol leucine were prepared in parallel generate a standard curve. The purple color formed upon incubation at 100° C. for 10 m was quantitated by dilution in 1:1 isopropanol/water, transferred to triplicate wells of a 96-well plate, and measurement of the $Abs_{570}$ on a microwell plate reader (Dynatech, Chantilly, Va.). The concentration of peptide was determined by a comparison to the standard curve and corrected for by the number of free amino groups that were associated with each peptide.

Example 2

Evaluation of Peptides Using in Vitro Bacterial Lysis Assays

Test Samples. The peptides used for this study are described and prepared as indicated above. The panel of bacterial isolates used for these experiments included both gram-positive and gram-negative clinical isolates. A given bacterial isolate was prepared as described below and exposed to a given eLLP as described below.

Bacterial lysis assay. Bacterial lysis assays were conducted in a manner similar to that described previously (Lehrer, R. I., M. E. Selsted, D. Szklarek, and F. J. 1983. Infect. Immun. 42: 10-4, 1983; Miller, M. A., R. F. Garry, J. M. Jaynes, and R. C. Montelaro, AIDS Res Hum Retroviruses 7: 511–519, 1991). Bacterial suspensions were cultured in Luria-Bertani Broth to mid-log growth phase and washed by two cycles of centrifugation and suspension in 10 mM phosphate buffer. The $Abs_{600}$ of the suspension was adjusted with 10 mM phosphate buffer such that, upon dilution, $5-10\times10^5$ cfu/mL would be treated in the assay. Bacteria were incubated for 1 h with two-fold dilutions of peptides (100 μM to 100 nM) in 96-well plates using 10 mM phosphate buffer, pH 7.2, as a diluent. Ten-fold dilutions of bacteria were performed to 1:1000; a 100 μl aliquot from each condition was spread on the surface of tryptic soy agar plates (Difco, Detroit, Mich.) which were incubated overnight. Colonies of surviving bacteria (cfu, colony-forming units) were counted and compared to untreated controls to determine the amount of peptide-induced killing under each condition. Log killing is defined as the log of the ratio of cfu present before and after treatment with peptide. The minimal bactericidal concentration, MBC, is the peptide concentration at which 99.9% (three log) killing is achieved (Pearson et al., Antimicrob. Agents *Chemother.* 18: 699–708, 1980).

Results. Representative gram positive (*S. aureus*) and gram negative (*P. aeruginosa*) clinical isolates were used as the index bacteria to survey the peptides described in this invention. Killing curves of LL37 and WLSA-5 (SEQ ID NO:3) for *S. aureus* and *P. aeruginosa* are shown in FIGS. 3 and 4. These results were reflective of the other peptides described in this invention. This analysis demonstrated that the eLLPs and LBUs were as effective as killing the index bacteria as the host derived antimicrobial peptide, LL37.

A limitation of many host-derived antimicrobial peptides is their decreased activity at physiologic (150 mM) NaCl concentration. See Friedrich et al., *Antimicrobial Agents and Chemotherapy* 43:1542–1548. The peptides WLSA-5 (SEQ ID NO:3) and LL37 were tested against the two index strains at physiologic NaCl. The results of these experiments are shown in FIGS. 5 and 6. The results of these experiments demonstrated that WLSA-5 (SEQ ID NO:3) was not influenced by NaCl in the same way as LL37 when *S. aureus* was used as the test bacterium. *P. aeruginosa* killing was not affected by NaCl inclusion for either peptide. These analyses suggest that the eLLPs are not as sensitive to the presence of ions as host derived antimicrobial peptides. The activity of eLLPs and LBUs of this invention were compared to an expanded list of clinical bacterial isolates. These are summarized in Table 2 by comparing their MBCs in phosphate buffer alone (low salt) and phosphate buffer containing 150 mM NaCl (physiologic conditions). Inspection of this table would lead one skilled in the art to conclude that the activity of eLLPs and LBUs compare favorably to the host derived antimicrobial peptides as it relates to the spectrum and potency of antimicrobial activity.

Example 3

Cystic Fibrosis Cell Culture Model of Selective Toxicity

Preparation of bacterial cells. *Burkholderia cepacia* and *P. aeruginosa* isolates were obtained from clinical microbiology laboratories and assayed using the broth dilution method as described in Example 2.

Preparation of eukaryotic cells. Differentiated primary cell cultures of human bronchial epithelial (HBE) cells (CF and non-CF) on an air-liquid interface were prepared in antibiotic free media. See Zabner, J. et al., 1996, *J Virol.* 70:6994–7003. These filters were incubated with *P. aeruginosa* followed by washing to remove non-adherent bacteria. Individual filters were next exposed to peptide at increasing concentrations. In order to release viable bacteria, trypsin/EDTA was added and these preparations were plated on standard bacteriologic media to quantify bacterial survival. Similarly prepared cells were monitored for peptide toxicity by measuring transepithelial resistance. The advantage of this model is that it can measure the selective toxicity of peptide for bacterium versus host cells under identical conditions.

Results. LLP-1 and its derivatives, SA-5 (SEQ ID NO:1), LSA-5 (SEQ ID NO:2) and WLSA-5 (SEQ ID NO:3) were tested for their bactericidal activity against pathogens typically associated with CF airway disease, namely, *S. aureus*, *P. aeruginosa*, and *B. cepacia*. Low (10 mM Phosphate buffer (PB)) and physiologic salt (10 mM PB containing 150 mM NaCl) concentrations were used as variable conditions under which peptide activity was tested using the standard broth dilution assay described in Example 2. Kill curves similar to those demonstrated in FIGS. 3–6 were generated and MBC values determined as described above. The MBC values for *S. aureus*, and *P. aeruginosa* are summarized in Table 2. Of the peptides tested, WLSA-5 (SEQ ID NO:3) maintained its activity in low and physiologic salt conditions against these two index strains.

WLSA-5 (SEQ ID NO:3) was tested and compared with LSA-5 (SEW ID NO:2) for activity against *B. cepacia*, an important bacterial pathogen associated with CF airway disease. As shown in FIG. 7, WLSA-5 (SEQ ID NO:3) was significantly more active than LSA-5 (SEQ ID NO:2) against *B. cepacia*. It has been generally reported that this organism is resistant to the activity of most antimicrobial peptides so the finding that WLSA-5 (SEQ ID NO:3) demonstrated significant in vitro activity. To test whether this activity was specific for the clinical isolate of *B. cepacia* tested in FIG. 7 or generally applicable to diverse *B. cepacia* isolates, a survey study was designed. For this study a collection of well-characterized *B. cepacia* genomovars were obtained and tested for susceptibility to killing by 25 $\mu$M WLSA-5 (SEQ ID NO:3). This was compared to the host antimicrobial peptide, LL37, at the identical concentration. The data shown in FIG. 8, is represented as the number of organisms surviving after treatment under these conditions. The results demonstrated that WLSA-5 (SEQ ID NO:3) was equal to or better than LL-37 at killing all bacterial strains within this collection. This finding suggests that WLSA-5 (SEQ ID NO:3) may be effective when administered in a CF setting where *B. cepacia* is the principal etiologic agent precipitating lung disease in CF patients.

Based on above in vitro findings, WLSA-5 (SEQ ID NO:3) was tested in a scenario that more accurately assessed its selective toxicity. For this assay, a cell culture model of bacterial adherence was established that utilized differentiated primary human airway epithelial cells. These cells were exposed to a standard inoculum of *P. aeruginosa* and bacteria and epithelial cells in co-culture were treated with different concentrations of test peptide. The ability of peptide to kill bacteria is monitored as a function of viable bacteria associated with the epithelial cells after peptide exposure. In order to assess epithelial cell toxicity, measurements of transepithelial resistance were performed. Differentiated airway epithelial cells in culture form tight junctions that are refractory to electrical current unless the monolayer is compromised by an event such as epithelial cell damage. Thus measurement of transepithelial resistance can be used as a sensitive measure of peptide toxicity. FIG. 9 depicts the results of an experiment in which increasing concentrations of WLSA-5 (SEQ ID NO:3) were added to bound *P. aeruginosa* and epithelial cells in co-culture. A decrease in bacterial viability and increase in transepithelial resistance (Rte) was demonstrated as a function of peptide concentration. A decrease in bacterial counts by two orders of magnitude resulted in a change in transepithelial resistance of less than 50%. Furthermore, the effect of WLSA-5 (SEQ ID NO:3) on transepithelial resistance was transient and not significantly different from LL-37. These data suggest that WLSA-5 (SEQ ID NO:3) demonstrates selective bacterial toxicity in a CF setting.

Example 4

Rabbit Joint Model of Septic Arthritis

We have demonstrated that LSA-5 (SEQ ID NO:2) is highly active against *S. aureus* (Table 2) and *S. epidermidis* in vitro, two common causes of joint infections, and can function in the presence of biologic fluids such as that derived from the joint synovium (FIG. 10), although the presence of synovial fluid clearly impairs the activity of LSA-5 (SEQ ID NO:2). We have extended these findings to a septic arthritis animal model. In this study joint sepsis was induced by inoculating one knee of a 2.5 Kg New Zealand white rabbit with $1 \times 10^5$ colony forming units of a clinical *S. aureus* isolate, a strain resistant to penicillin but sensitive to methicillin, cephalosporins, and clindamycin. Using this model, symptoms of septic arthritis (e.g., degradation of the synovium) were monitored and the ability of antimicrobial agents to limit the degeneration of the joint post-infection can be assessed. In this application the bacterial infection is allowed to establish for 1 h. At this point the joint was accessed and increasing concentrations of LSA-5 (SEQ ID NO:2) (0, 50, 100, and 200 $\mu$M) in phosphate buffer (PB) was administered intraarticularly. The concentration of bacteria associated with joint fluid was established at time 0 and 1 h post LSA-5 (SEQ ID NO:2) instillation by plating dilutions of the synovial fluid on LB agar. The results of this experiment demonstrated a dose-dependent decrease in colony forming units compared to the non-peptide treated joint when examined after 1 h (FIG. 11).

In order to demonstrate that successive doses of LSA-5 (SEQ ID NO:2) can be efficacious for limiting bacterial load in this rabbit model, administration of two peptide treatments of 150 $\mu$M LSA-5 (SEQ ID NO:2) at times 0 and 1 h was evaluated. Measurement of the bacterial load 1 h post-treatment demonstrated a significant decrease in the peptide treated joints when compared to joints treated with phosphate buffer in the absence of peptide. This was compared with multiple injections of a standard 0.35% neomycin or a combination of neomycin and LSA-5 (SEQ ID NO:2). Administration of each of these formulations was performed intraarticularly at time 0,1, and 2 h. The results of this experiment demonstrated that when compared to groups treated with LSA-5 (SEQ ID NO:2)or neomycin alone, substantially fewer bacteria were recovered from the joint treated with the of LSA-5/neomycin combination (FIG. 12). Furthermore, in all of these animal experiments no adverse toxicity was observed when peptide was administered alone. These data mimic chronic infection associated with septic arthritis and suggest that topical treatment can be initially effective.

One potentially important application for the eLLPs as it relates to septic arthritis is their activity when bound to a solid phase substrate such as a prosthetic joint. To address this, the amino terminal group of LSA-5 (SEQ ID NO:2) was covalently attached to an Affigel™ 15 (BioRad, Hercules, Calif.) resin. This permeable solid support was placed in a small column and exposed to 1 mL suspension of a×$10^6$ bacteria/mL. The solution was allowed to pass by gravity through the column and the eluant collected and quantitated for the number of viable bacteria. As a negative control, an identical column was prepared except that a non-antimicrobial peptides was attached in place of LSA-5 (SEQ ID NO:2). The results are summarized in Table 3 below and demonstrate that either a suspension of *P. aeruginosa* or *S. aureus* were completely sterilized by exposure to the column. In contrast, no reduction in viable bacteria was observed after exposure to the non-antimicrobial peptide control column. Furthermore, the same LSA-5 (SEQ ID NO:2) column could be repeatedly exposed to bacterial suspensions and it maintained activity for up to 6 passages. These data suggest the possibility that prosthetic joints could be coated with the eLLPs of the present invention to inhibit the nucleation of biofilm formation observed in joint replacement surgery which leads to septic arthritis.

TABLE 3

|  | Input Bacteria | | | |
|---|---|---|---|---|
|  | P. aeruginosa | | S. aureus | |
| Peptide | LSA-5 | Control | LSA-5 | Control |
| Bacterial count prior to column exposure | 1 × 10$^6$ | 1 × 10$^6$ | 1 × 10$^6$ | 1 × 10$^6$ |
| Bacterial count from eluant | 0 | 1 × 10$^6$ | 0 | 1 × 10$^6$ |

Example 5

Suppression of HIV-1 Infectivity

Based on the observation that the peptides of this invention were active against certain eukaryotic cell membranes (e.g., demonstrated to lyse erythrocytes) it was reasoned that peptides of this invention may be active in suppressing the infectivity of enveloped viruses. Proof for this concept was obtained by studying the ability of an LLP1 peptide, LSA-5 (SEQ ID NO:2) to inhibit the infectivity of HIV-1 similar to that previously shown for cationic host-derived antimicrobial peptides (Wachinger, M., et al. (1998) *Journal of General Virology* 79: 731–40; Wachinger, M., T. Saermark and V. Erfle (1992) *FEBS Letters* 309:235–41; Robinson, W. E., Jr., B. McDougall, D. Tran and M. E. Selsted (1998) *Journal of Leukocyte Biology* 63:94–100; Yasin, B. et al. (2000) *European Journal of Clinical Microbiology & Infectious Diseases* 19:187–94).

In this example human peripheral blood monocytes (PBMCs) were obtained from healthy volunteers and maintained in culture at a concentration of 1×10$^5$ viable cells per mL of medium. These cells were stimulated by the addition of phytohemagglutinin (PHA). To this a standardized titer of purified HIV-1 (strain IIIB) virions was added to PBMCs to generate a p24 antigen signal of 14,000 pg/mL five days post exposure to virus.

In order to test whether the LLP peptide, LSA-5 (SEQ ID NO:2) was able to suppress HIV-1 activity, LSA-5 at concentrations ranging between 0.1 and 100 µM were incubated with the standard virus titer determined as above for 30 min. Virions surviving peptide exposure were isolated by ultracentrifugation at 100,000×g for 60 min. Viral pellets were used to infect PHA stimulated PBMCs prepared as described above. Five days post infection the level of p24 antigen was determined and compared to a non-peptide treated control. The data was expressed as the ratio of p24 antigen associated with peptide-treated vs. non-peptide treated HIV-1 infected cells to obtain a value referred to as percent suppression.

Figure 13:
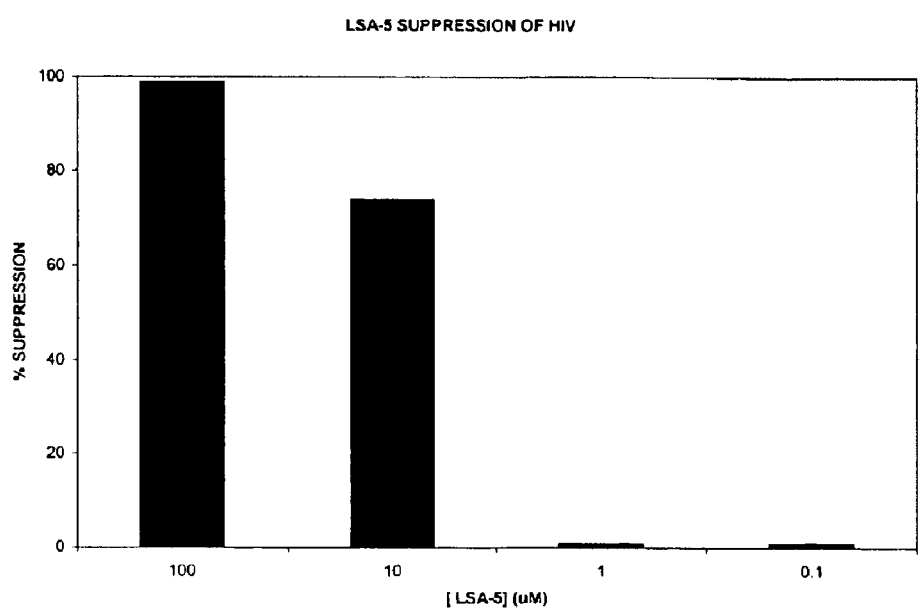
FIG. 13 shows a bar graph which illustrates that an exemplary embodiment of the peptides of the present invention, LSA-5, has anti-HIV1 activity.

As shown in FIG. 13, LSA-5-treated virions alone at 100 µM reduced HIV-1 infectivity by nearly 100%. At 10 µM, HIV-1 infectivity was reduced by 75%. At 1 and 0.1 µM there is a drop off this inhibitory activity of LSA-5. Experiments not described herein employing other peptides described by this invention demonstrate that those peptides observed to have a high hemolytic activity for red cells were more active on a molar basis against HIV-1 virions than those with low hemolytic activity. These data demonstrate that the LLP peptides of the present invention are active against enveloped viruses, and particularly, HIV-1, and can be engineered for increased potency in this setting.

We claim:

1. An isolated and purified having an amino acid sequence selected from the group consisting of:
RVVRVVRRVVRR (SEQ ID NO:4);
RRVVRRVRRVVRRVVRVVRRVVRR (SEQ ID NO:5);
VRRVVRRVVRVVRRVVRRVRRVVRRV-VRVVRRVVRR (SEQ ID NO:6);
RRVVRRVRRVVRRVVRVVRRVVRRVRRV-VRRVVRVVRRVVRR (SEQ ID NO:7);
RVVRVVRRVVRRVRRVVRRVVRVVRRV-VRRVRRVVRRVVRVVRRV VRR (SEQ ID NO:8);
RVVRVVRRWVRR (SEQ ID NO:9);
RRWVRRVRRVWRRVVRVVRRWVRR (SEQ ID NO:10);
VRRVWRRVVRVVRRWVRRVRRVWRRV-VRVVRRWVRR (SEQ ID NO:11); and
RVVRVVRRWVRRVRRVWRRVVRVVR-RWVRRVRRVWRRVVRVVRR WRVV (SEQ ID NO:12).

2. The peptide of claim 1 having the amino acid sequence: RVVRVVRRVVRR (SEQ ID NO:4).

3. A composition comprising the peptide of claim 2 and a carrier.

4. The peptide of claim 1 having the amino acid sequence: RRVVRRVRRVVRRVVRVVRRVVRR (SEQ ID NO:5).

5. A composition comprising the peptide of claim 4 and a carrier.

6. The peptide of claim 1 having the amino acid sequence: VRRVVRRVVRVVRRVVRRVRRVVRRV-VRVVRRVVRR (SEQ ID NO:6).

7. A composition comprising the peptide of claim 6 and a carrier.

8. The peptide of claim 1 having the amino acid sequence: RRVVRRVRRVVRRVVRVVRRVVRRVRRV-VRRVVRVVRRVVRR (SEQ ID NO:7).

9. A composition comprising the peptide of claim 8 and a carrier.

10. The peptide of claim 1 having the amino acid sequence: RVVRVVRRVVRRVRRVVRRVVRVVRRV-VRRVRRVVRRVVRVVRRV VRR (SEQ ID NO:8).

11. A composition comprising the peptide of claim 10 and a carrier.

12. The peptide of claim 1 having the amino acid sequence: RVVRVVRRWVRR (SEQ ID NO:9).

13. A composition comprising the peptide of claim 12 and a carrier.

14. The peptide of claim 1 having the amino acid sequence: RRWVRRVRRVWRRVVRVVRRWVRR (SEQ ID NO:10).

15. A composition comprising the peptide of claim 14 and a carrier.

16. The peptide of claim 1 having the amino acid sequence: VRRVWRRVVRVVRRWVRRVRRVWRRV-VRVVRRWVRR (SEQ ID NO:11).

17. A composition comprising the peptide of claim 16 and a carrier.

18. The peptide of claim 1 having the amino acid sequence: RVVRVVRRWVRRVRRVWRRVVRVVR-RWVRRVRRVWRRVVRVVRR WRVV (SEQ ID NO:12).

19. A composition comprising the peptide of claim 18 and a carrier.

20. The peptide of claim 1 wherein said peptide has antimicrobial activity.

21. The peptide of claim 1 wherein said peptide has antimicrobial activity in a low salt medium.

22. The peptide of claim 1 wherein said peptide has antimicrobial activity in physiological salt.

23. An isolated and purified lentiviral lytic peptide-1 peptide analog-comprising an amino acid sequence selected from the group consisting of:
RVVRVVRRVVRR (SEQ ID NO:4);
RRVVRRVRRVVRRVVRVVRRVVRR (SEQ ID NO:5);
VRRVVRRVVRVVRRVVRRVRRVVRRV-VRVVRRVVRR (SEQ ID NO:6);
RRVVRRVRRVVRRVVRVVRRVVRRVRRV-VRRVVRVVRRVVRR (SEQ ID NO:7);
RVVRVVRRVVRRVRRVVRRVVRVVRRV-VRRVRRVVRRVVRVVRRV VRR (SEQ ID NO:8);
RVVRVVRRWVRR (SEQ ID NO:9);
RRWVRRVRRVWRRVVRVVRRWVRR (SEQ ID NO:10);
VRRVWRRVVRVVRRWVRRVRRVWRRV-VRVVRRWVRR (SEQ ID NO:11); and
RVVRVVRRWVRRVRRVWRRVVRVVR-RWVRRVRRVWRRVVRVVRR WRVV (SEQ ID NO:12),
and at least one additional residue wherein said peptide analog comprises an amphipathic α-helical structure.

24. A solid phase substrate comprising at least one peptide selected from the group consisting of:
RVVRVVRRVVRR (SEQ ID NO:4);
RRVVRRVRRVVRRVVRVVRRVVRR (SEQ ID NO:5);
VRRVVRRVVRVVRRVVRRVRRVVRRV-VRVVRRVVRR (SEQ ID NO:6);
RRVVRRVRRVVRRVVRVVRRVVRRVRRV-VRRVVRVVRRVVRR (SEQ ID NO:7);
RVVRVVRRVVRRVRRVVRRVVRVVRRV-VRRVRRVVRRVVRVVRRV VRR (SEQ ID NO:8);

RVVRVVRRWVRR (SEQ ID NO:9);

RRWVRRVRRVWRRVVRVVRRWVRR (SEQ ID NO:10);

VRRVWRRVVRVVRRWVRRVRRVWRRV-VRVVRRWVRR (SEQ ID NO:11); and

RVVRVVRRWVRRVRRVWRRVVRVVR-RWVRRVRRVWRRVVRVVRR WRVV(SEQ ID NO:12).

25. The solid phase substrate of claim 24 wherein said solid phase substrate is a prosthetic device.

26. The solid phase substrate of claim 24 wherein the prosthetic device is a prosthetic joint.

27. The peptide of claim 1 wherein said peptide further comprises at least one cysteine residue.

28. The peptide of claim 27 wherein said peptide is a disulfide linked dimeric peptide.

29. An isolated and purified peptide-cargo complex comprising a cargo and a peptide selected from the group consisting of:

RVVRVVRRVVRR (SEQ ID NO:4);

RRVVRRVRRVVRRVVRVVRRVVRR (SEQ ID NO: 5);

VRRVVRRVVRVVRRVVRRVRRVVRRV-VRVVRRVVRR (SEQ ID NO: 6);

RRVVRRVRRVVRRVVRVVRRVVRRVRRV-VRRVVRVVRRVVRR (SEQ ID NO:7);

RVVRVVRRVVRRVRRVVRRVVRVVRRV-VRRVRRVVRRVVRVVRRV VRR (SEQ ID NO:8);

RVVRVVRRWVRR (SEQ ID NO:9);

RRWVRRVRRVWRRVVRVVRRWVRR (SEQ ID NO:10);

VRRVWRRVVRVVRRWVRRVRRVWRRV-VRVVRRWVRR (SEQ ID NO:11); and

RVVRVVRRWVRRVRRVWRRVVRVVR-RWVRRVRRVWRRVVRVVRR WRVV (SEQ ID NO:12).

30. The peptide-cargo complex of claim 29 wherein said peptide has antimicrobial activity and said cargo increases the antimicrobial activity of said peptide.

* * * * *

UNITED STATES PATENT AND TRADEMARK OFFICE
CERTIFICATE OF CORRECTION

| | | |
|---|---|---|
| PATENT NO. | : 6,887,847 B2 | Page 1 of 1 |
| APPLICATION NO. | : 10/079075 | |
| DATED | : May 3, 2005 | |
| INVENTOR(S) | : Ronald C. Montelaro and Timothy A. Mietzner | |

It is certified that error appears in the above-identified patent and that said Letters Patent is hereby corrected as shown below:

Col. 27, lines 15 - 33
    Claim 1 An Isolated and purified <u>peptide</u> having an amino acid sequence selected from the group consisting of:
    RVVRVVRRVVRR (SEQ ID NO: 4);
    RRVVRRVRRVVRRVVRVVRRVVRR (SEQ ID NO: 5)
    VRRVVRRVVRVVRRVVRRVRRVVRRVVRVVRRVVRR (SEQ ID NO: 6)
    RRVVRRVRRVVRRVVRVVRRVVRRVRRVVRRVVRVVRRVVRR (SEQ ID NO:7);
    RVVRVVRRVVRRVRRVVRRVVRVVRRVVRRVRRVVRRVVRVVRRVVRR (SEQ ID NO: 8)
    RVVRVVRRWVRR (SEQ ID NO: 9);
    RRWVRRVRRVWRRVVRVVRRWVRR (SEQ ID NO: 10);
    VRRVWRRVVRVVRRWVRRVRRVWRRVVRVVRRWVRR (SEQ ID NO: 11); and
RVVRVVRRWVRRVRRVWRRVVRVVRRWVRRVRRVWRRVVRVVRRWRVV (SEQ ID NO: 12).

Signed and Sealed this

Twenty-fourth Day of April, 2007

JON W. DUDAS
*Director of the United States Patent and Trademark Office*